United States Patent
Fattom et al.

(10) Patent No.: US 10,206,996 B2
(45) Date of Patent: Feb. 19, 2019

(54) HERPES SIMPLEX VIRUS NANOEMULSION VACCINE

(75) Inventors: Ali I. Fattom, Ann Arbor, MI (US);
Jakub Simon, Ann Arbor, MI (US);
James R. Baker, Jr., Ann Arbor, MI (US); Tarek Hamouda, Milan, MI (US); Vira Bitko, Ann Arbor, MI (US)

(73) Assignee: NanoBio Corporation, Ann Arbor, MI (US)

( * ) Notice: Subject to any disclaimer, the term of this patent is extended or adjusted under 35 U.S.C. 154(b) by 0 days.

(21) Appl. No.: 13/591,775

(22) Filed: Aug. 22, 2012

(65) Prior Publication Data

US 2013/0052235 A1 Feb. 28, 2013

Related U.S. Application Data

(60) Provisional application No. 61/526,023, filed on Aug. 22, 2011.

(51) Int. Cl.
| | |
|---|---|
| *A61K 39/00* | (2006.01) |
| *A61K 39/245* | (2006.01) |
| *A61K 39/39* | (2006.01) |
| *A61K 9/107* | (2006.01) |
| *A61K 39/12* | (2006.01) |

(52) U.S. Cl.
CPC .......... *A61K 39/245* (2013.01); *A61K 9/1075* (2013.01); *A61K 39/12* (2013.01); *A61K 39/39* (2013.01); *A61K 2039/55555* (2013.01); *A61K 2039/55566* (2013.01); *C12N 2710/16634* (2013.01)

(58) Field of Classification Search
None
See application file for complete search history.

(56) References Cited

U.S. PATENT DOCUMENTS

| | | | |
|---|---|---|---|
| 4,826,687 A | 5/1989 | Nerome et al. | |
| 4,895,452 A | 1/1990 | Yiournas et al. | |
| 5,103,497 A | 4/1992 | Hicks | |
| 5,171,568 A | 12/1992 | Burke et al. | |
| 5,612,041 A | 3/1997 | Burke et al. | |
| 5,747,039 A * | 5/1998 | Burke et al. | 424/186.1 |
| 5,962,298 A | 10/1999 | Fiers et al. | |

(Continued)

FOREIGN PATENT DOCUMENTS

| | | |
|---|---|---|
| WO | WO 98/33487 | 8/1998 |
| WO | WO 2004/030608 A2 | 4/2004 |

(Continued)

OTHER PUBLICATIONS

Kwant and Rosenthal. Intravaginal immunization with viral subunit protein plus CpG oligodeoxynucleotides induces protective immunity against HSV-2. Vaccine. Aug. 13, 2004;22(23-24):3098-104. (Year: 2004).*

(Continued)

*Primary Examiner* — Michelle S Horning
(74) *Attorney, Agent, or Firm* — Foley & Lardner LLP

(57) ABSTRACT

The present application relates to the field of human immunology, in particular, a herpes simplex virus (HSV) vaccine. The subunit vaccine composition comprises isolated surface glycoproteins from herpes simplex viruses, fusion proteins or fragments thereof mixed in varied combination with a nanoemulsion, which is a potent immune enhancer.

28 Claims, 1 Drawing Sheet

(56) References Cited

U.S. PATENT DOCUMENTS

| | | | |
|---|---|---|---|
| 6,015,832 A | 1/2000 | Baker, Jr. et al. | |
| 6,027,730 A | 2/2000 | Francotte et al. | |
| 6,146,632 A | 11/2000 | Momin et al. | |
| 6,194,546 B1 | 2/2001 | Newton et al. | |
| 6,372,227 B1 | 4/2002 | Garcon et al. | |
| 6,375,952 B1 | 4/2002 | Koelle et al. | |
| 6,451,325 B1 | 9/2002 | Van Nest et al. | |
| 6,506,803 B1 | 1/2003 | Baker, Jr. et al. | |
| 6,559,189 B2 | 5/2003 | Baker, Jr. et al. | |
| 6,623,739 B1 | 9/2003 | Momin et al. | |
| 6,635,676 B2 | 10/2003 | Baker, Jr. et al. | |
| 6,692,752 B1 | 2/2004 | Slaoui et al. | |
| 6,861,244 B2 | 3/2005 | Barrett et al. | |
| 6,867,000 B2 | 3/2005 | Mishkin et al. | |
| 7,192,595 B2 | 3/2007 | Arnon et al. | |
| 7,314,624 B2 | 1/2008 | Baker et al. | |
| 7,323,182 B2 | 1/2008 | Garcon et al. | |
| 7,357,936 B1 | 4/2008 | Garcon | |
| 7,731,967 B2 | 6/2010 | O'Hagan et al. | |
| 8,226,965 B2 | 7/2012 | Baker, Jr. et al. | |
| 8,541,002 B2* | 9/2013 | Truneh et al. | 424/196.11 |
| 9,238,683 B2* | 1/2016 | Zhu | C07K 14/005 |
| 2002/0058047 A1 | 5/2002 | Garcon et al. | |
| 2004/0043041 A1 | 3/2004 | Baker, Jr. et al. | |
| 2004/0151734 A1 | 8/2004 | Slaoui et al. | |
| 2005/0208083 A1 | 9/2005 | Annis | |
| 2006/0251684 A1 | 11/2006 | Annis et al. | |
| 2007/0054834 A1 | 3/2007 | Baker | |
| 2008/0181949 A1 | 7/2008 | Baker et al. | |
| 2008/0299140 A1 | 12/2008 | Georges et al. | |
| 2009/0269394 A1 | 10/2009 | Baker, Jr. et al. | |
| 2010/0075914 A1 | 3/2010 | Flack et al. | |
| 2010/0092526 A1 | 4/2010 | Baker, Jr. et al. | |
| 2010/0226983 A1 | 9/2010 | Sutcliffe et al. | |
| 2011/0177125 A1 | 7/2011 | Friedman et al. | |
| 2011/0200657 A1 | 8/2011 | Baker | |
| 2012/0064136 A1 | 3/2012 | Baker, Jr. et al. | |
| 2012/0171249 A1 | 7/2012 | Annis et al. | |
| 2012/0219602 A1* | 8/2012 | Flack et al. | 424/400 |

FOREIGN PATENT DOCUMENTS

| | | | |
|---|---|---|---|
| WO | WO 2004/087204 A2 | 10/2004 | |
| WO | WO 2009/129470 A2 | 10/2009 | |
| WO | WO 2009/131995 A1 | 10/2009 | |

OTHER PUBLICATIONS

Extended European Search Report issued in related European Patent Application No. 12 82 5300, dated Mar. 5, 2015.

Allen S, et al., Immunization with different viral antigens alters the pattern of T cell exhaustion and latency in herpes simplex virus type-1 infection mice. J Virol. 2010. 84:12315-12324.

Ashley, et al. Humoral immune response to herpes simplex virus type 2 glycoproteins in patients receiving a glycoprotein subunit vaccine. J Virol. 1985. 56:475-481.

Awasthi, et al., Immunization with HSV-1 glycoprotein C prevents immune evasion from complement and enhances the efficacy of an HSV-1 glycoprotein D subunit vaccine. Vaccine. 2009. 27:6845-6853.

Awasthi, et al., HSV-2 glycoprotein C subunit immunization with glycoprotein D improves the protection of dorsal root ganglia in mice and reduces the frequency of recurrent vaginal shedding of HSV-2 DNA in guinea pigs compared to glycoprotein D alone. J. Virol. 2011, pp. 10472-10486.

Bernstein, et al., Effects of herpes simplex virus type 2 glycoprotein vaccines and CLDC adjuvant on genital herpes infection in the guinea pig. Vaccine. 2011. 29:2071-2078.

Bielinska, A, Gerber M, Blanco L, et al. Induction of Th17 cellular immunity with a novel nanoemulsion adjuvant. 2010. Crit Rev Immunol. 30:189-199.

Chan T, Barra N, et al. Innate and adaptive immunity against herpes simplex virus type 2 in the genital mucosa. J Repro Immunol. 2011. 88:210-218 (Abstract).

Chang, YJ, Jiang M, Lubinski, J., et al. Implication for herpes simplex virus strategies based on antibodies produced to herpes simplex virus type 1 glycoprotein gC immune evasion domains. Vaccine. 2005. 23:4658-4665.

Conti HR, Shen F, et al., Th17 and IL-17 receptor signaling are essential for mucosal host defenses against oral candidiasis. J Exp Med. 2009. 206:299-311.

Corey, et al., Recombinant glycoprotein vaccine for the prevention of genital HSV-2 infection; two randomized controlled trials. JAMA. 1999. 281:331-340.

Dasgupta, G, BenMohamed, L. of mice and humans: how reliable are animal models for evaluation of herpes CD8+-T cells epitopes-based immunotherapeutic vaccine candidates. Vaccine. 2011. 29:5824-5836.

Dasgupta, G, Chentoufi A, Nesburn A, et al. New concepts in herpes simplex virus vaccine development: notes from the battlefield. Expert Rev Vaccine. 2009. 8:1023-1035.

DeLyrica E, Raymond WR, et al., Vaccination of mice with H pylori induces a strong Th-17 response and immunity that is neutrophil dependent. Gastroent. 2009. 136:247-256.

Ghiasi, H, Kaiwar R., et al. Baculovirus-expressed glycoprotein E (gE) of herpes simplex virus type 1 (HSV-1) protects mice from lethal intraperitoneal and lethal ocular HSV-1 challenge. 1992. Virol. 188:469-476.

Hamouda T, Chepurnov A, Mank N, et al. Efficacy, immunogenicity and stability of a novel intranasal nanoemulsion adjuvanted influenza vaccine in a murine model. Hum Vaccine. 2010. 6:585-594.

Han J, et al., It is time to examine the role of host cytokine response in neonatal herpes simplex virus infection. Future Virol. 2011. 6:679-681.

Judson, K, Lubinski, J, Jiang, M, et al. Blocking immune evasion as a novel approach for prevention and treatment of herpes simplex virus infection. J. Virol. 2003. 77:12639-12645.

Lindell D, Morris S, White M, et al. A novel inactivated intranasal respiratory syncytial virus vaccine promotes viral clearance without Th2 associated vaccine-enhanced disease. PLoS One. 2011. 7:e21823, 14 pages.

Makidon et al., "Pre Clinical Evaluation of a Novel Nanoemulsion-Based Hepatitis B Mucosal Vaccine," *PLoS One*, vol. 3, No. 8, pp. 2954; 1-15 (2008).

McGowin C, Pyles R. Mucosal treatment for herpes simplex virus: insights on targeted immunoprophylaxis and therapy. Future Microbiol. 2010. 5:15-22.

Parr E, Parr M. Immune response and protection against vaginal infection after nasal or vaginal immunization with attenuated herpes simplex virus type-2. Immunol. 1999. 98:639-645.

Thatte A, DeWitte-Orr J, Lichty K, et al. A critical role for IL-15 in TLR-mediated innate antiviral immunity against genital HSV-2 infection. Immunol and Cell Biol. 2011. 1-7 (Abstract).

Zarling, J, Moran P, et al. Herpes Simplex Virus (HSV)-specific proliferative and cytotoxic T-cell responses in humans immunized with an HSV type 2 glycoprotein subunit vaccine. J Virol. 1988. 62:4481-4485.

Dobson CB, Itzhaki RF (1999). "Herpes simplex virus type 1 and Alzheimer's disease". Neurobiol. Aging 20 (4): 457-65 (Abstract).

Pyles RB (Nov. 2001). "The association of herpes simplex virus and Alzheimer's disease: a potential synthesis of genetic and environmental factors" (PDF). Herpes 8 (3): 64-8.

Office Action issued in related European Patent Application No. 12825300.2, dated Dec. 16, 2015.

Notice of Reasons for Rejection issued in related Japanese Patent Application No. 2014-527252, dated May 31, 2016.

European Communication issued in related European Patent Application No. 12825300.2, dated Jun. 16, 2016.

Morello, et al., "Immunization with Herpes Simplex Virus 2 (HSV-2) Genes plus Inactivated HSV-2 is Highly Protective against Acute and Recurrent HSV-2 Disease," Journ. of Virology, vol. 85, No. 7, pp. 3461-3472 (2011).

Corey et al., "Once-daily Valacyclovir to reduce the risk of transmission of genital Herpes," N. Engl. J. Med., vol. 350, No. 1, pp. 11-20 (2004).

(56) References Cited

OTHER PUBLICATIONS

Epidemiology of Herpes Simplex, 6 pages (retrieved on Jan. 2, 2015).
Montanide ISA 720 VG, SEPPIC, retrieved from the Internet on Jan. 3, 2016, 1 page.
Montanide ISA, SEPPIC, retrieved from the Internet on Mar. 14, 2016, 1 page.
Emulsion, retrieved from the Internet on Mar. 14, 2016, 8 pages.
Emulsion types, retrieved from the Internet on Mar. 14, 2016, 4 pages.
Baumeister et al., "Superior Efficacy of Helicase-Primase Inhibitor BAY 57-1293 for herpes infection and latency in the guinea pig model of human genital herpes disease," *Antiviral Chemistry & Chemotherapy*, vol. 18, No. 1, pp. 35-48 (2007).
McClements et al., "Immunization with DNA vaccines encoding glycoprotein D or glycoprotein B, alone or in combination, induces protective immunity in animal models of herpes simplex virus-2 disease," *Proc. Natl. Acad. Sci.*, vol. 93, pp. 11414-11420 (1996).
Notice of Reasons for Rejection issued in related Japanese Patent Application No. 2014-527252, dated Jan. 24, 2017.
Office Action issued in co-pending Canadian Patent Application No. 2,845,872, dated Jul. 6, 2018.

\* cited by examiner

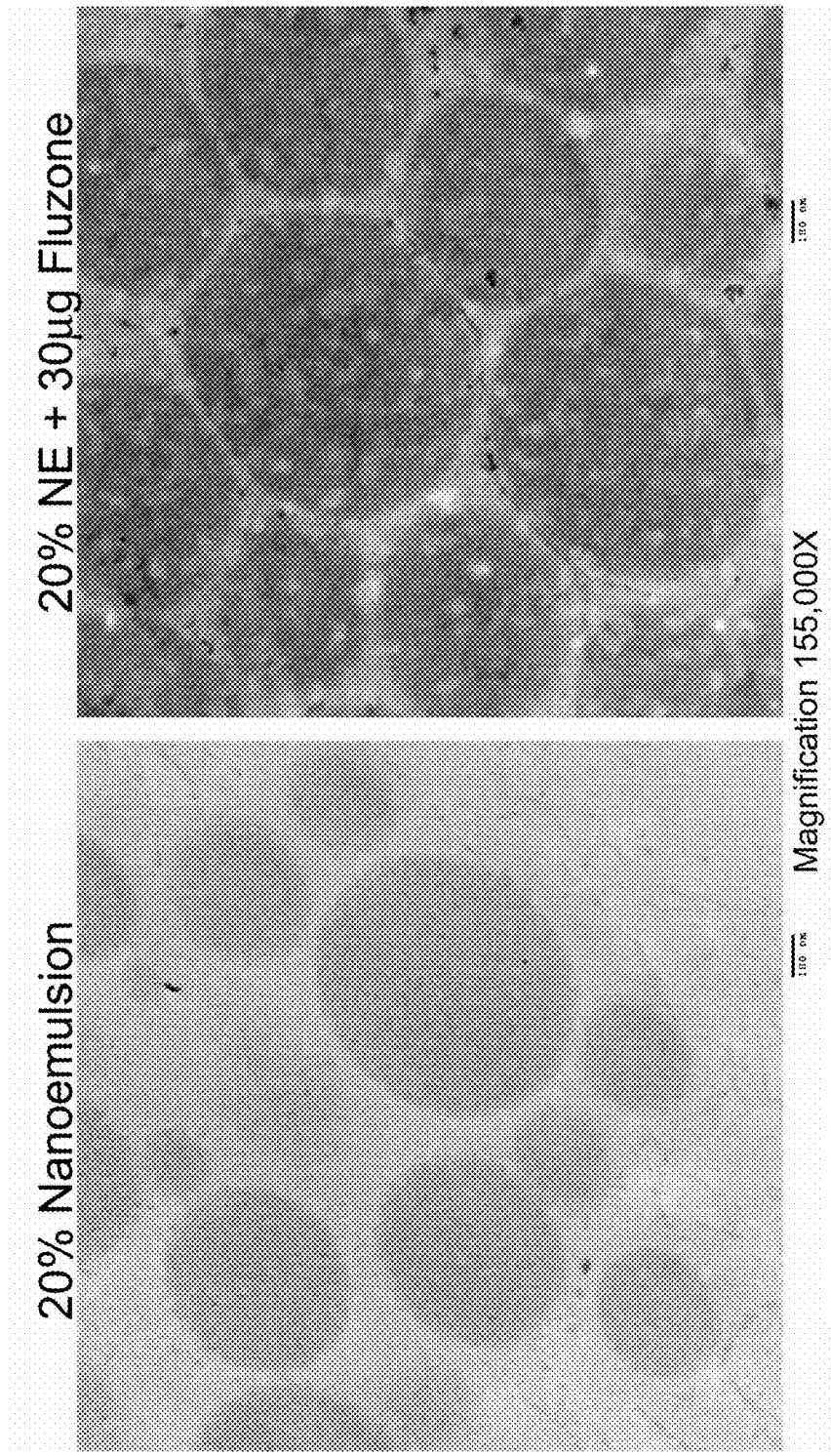

HERPES SIMPLEX VIRUS NANOEMULSION VACCINE

CROSS-REFERENCE TO RELATED APPLICATION

This application claims benefit of U.S. Provisional Application No. 61/526,023, filed on Aug. 22, 2011, which is specifically incorporated by reference.

FIELD OF THE INVENTION

The present application relates to the field of human immunology, in particular, a herpes simplex virus (HSV) vaccine. The vaccine composition comprises isolated whole HSV virus, either native or mutant, and/or isolated surface glycoproteins from herpes simplex viruses, such as gB, gC, gD and gE glycoproteins, fusion proteins or fragments thereof. The whole virus and/or isolated surface glycoproteins are mixed in varied combination with a nanoemulsion, which is a potent immune enhancer. The vaccine, comprising an oil-in-water nanoemulsion and HSV antigens, induces an activated and broad-based humoral and cellular immune response comprising the induction of neutralizing antibodies, Th1, Th2 and Th17 arms of the immune response.

BACKGROUND OF THE INVENTION

Herpes simplex virus types 1 and 2 are major human pathogens that primarily cause infections of the oral-facial, ocular or genital mucosal areas, and establish lifelong infections that can result in reactivation at the respective mucosal sites where the primary infection was initiated (Roizman and Spears, 1996). HSV-1 appears to be particularly damaging to the nervous system and increases the risk of developing Alzheimer's disease. The HSV virus interacts with the components and receptors of lipoproteins, which may lead to the development of Alzheimer's disease. (Dobson and Itzhaki, 1999.) This research identifies HSVs as the pathogen most clearly linked to the establishment of Alzheimer's. (Pyles R B, November 2001). A major strategy to break the cycle of transmission is the potential usage of an effective vaccine as a prophylaxis method of choice for controlling the spread of HSV.

Extensive studies have been conducted on HSV replication and pathogenesis, in particular in animal models. A variety of vaccine strategies have been tested in varied animal models, including subunit and whole virus vaccines, with encouraging results (Awasthi et al., 2011; Bernstein et al, 2011; Chan et al., 2011). However, clinical trials in humans with HSV vaccines have met with limited success (Corey et al., 1999; Ashley et al., 1985; Zarling et al., 1988). A consensus on the optimal vaccine needs to engage all the respective arms of the immune response, including Th1, Th2 and Th17 along with the presence of neutralizing antibodies, and mucosal antibodies (IgA).

Subunit vaccines have been tested utilizing individual HSV surface antigens, including gB (Allen et al, 2010), gC (Awasthi et al, 2009; Chang et al., 2005), gD (Bernstein et al., 2010) and gE (Ghiasi et al., 2992). In addition, whole HSV attenuated vaccine and subunit vaccines when tested in humans did not produce sufficient mucosal antibodies (IgA) at the appropriate surfaces, in addition T cell responses was lower that the mucosal surfaces, which is important for HSV infections and potential reactivation (Parr and Parr, 1999).

In the various HSV immunization studies, the use of the appropriate animal model is important to replicate the natural pathogenic process, as Th1 immune response is a crucial component for protection against potential reinfection and viral reactivation (Dasgupta et al., 2011).

The lack of an adequate vaccine for human use prompted the inventors to elaborate on previous findings regarding the novel features of a nanoemulsion as an immune enhancer for antigens. Use of traditional adjuvant has been added to HSV subunit vaccines without apparent efficacy in the clinical settings (Bernstein et al., 2011; Corey et al., 1999; Dasgupta et al., 2011; Ashley et al., 1985). However, a nanoemulsion, whilst providing an adjuvant effect, also helps in antigen presentation by attracting the appropriate cell types and activating multiple arms of the immune response. (Hamouda et al., 210; Bielinska et al., 2010; Makidon et al., 2008).

As with most vaccines, greater immunogenicity is also sought as it correlates with greater efficacy in humans. The prior art has typically disclosed the use of recombinant proteins (e.g., U.S. Pat. Nos. 7,192,595; 6,194,546; 5,962,298), as well as the addition of adjuvants such as aluminum (U.S. Pat. No. 6,861,244) and muramyldipeptide (U.S. Pat. No. 4,826,687) to compositions to increase the immunogenicity. However, there still exists a need to develop highly effective HSV vaccines with improved storage stability and ease of administration, which are characteristics of the nanoemulsion vaccines of the present invention.

Prior teachings related to nanoemulsions are described in U.S. Pat. No. 6,015,832, which is directed to methods of inactivating Gram-positive bacteria, a bacterial spore, or Gram-negative bacteria. The methods comprise contacting the Gram-positive bacteria, bacterial spore, or Gram-negative bacteria with a bacteria-inactivating (or bacterial-spore inactivating) emulsion. U.S. Pat. No. 6,506,803 is directed to methods of killing or neutralizing microbial agents (e.g., bacterial, virus, spores, fungus, on or in humans using an emulsion. U.S. Pat. No. 6,559,189 is directed to methods for decontaminating a sample (human, animal, food, medical device, etc.) comprising contacting the sample with a nanoemulsion. The nanoemulsion, when contacted with bacteria, virus, fungi, protozoa or spores, kills or disables the pathogens. The antimicrobial nanoemulsion comprises a quaternary ammonium compound, one of ethanol/glycerol/PEG, and a surfactant. U.S. Pat. No. 6,635,676 is directed to two different compositions and methods of decontaminating samples by treating a sample with either of the compositions. Composition 1 comprises an emulsion that is antimicrobial against bacteria, virus, fungi, protozoa, and spores. The emulsions comprise an oil and a quaternary ammonium compound. U.S. Pat. No. 7,314,624 is directed to methods of inducing an immune response to an immunogen comprising treating a subject via a mucosal surface with a combination of an immunogen and a nanoemulsion. The nanoemulsion comprises oil, ethanol, a surfactant, a quaternary ammonium compound, and distilled water. US-2005-0208083 and US-2006-0251684 are directed to nanoemulsions having droplets with preferred sizes. US-2007-0054834 is directed to compositions comprising quaternary ammonium halides and methods of using the same to treat infectious conditions. The quaternary ammonium compound may be provided as part of an emulsion. US-2007-0036831 and US 2011-0200657 are directed to nanoemulsions comprising an anti-inflammatory agent. Other publications that describe nanoemulsions include U.S. Pat. No. 8,226,965 for "Methods of treating fungal, yeast and mold infections;" US 2009-0269394 for "Methods and compositions for treating onychomycosis;" US 2010-0075914 for "Methods for treating herpes virus infections;" US 2010-0092526 for "Nanoemulsion therapeutic compositions and methods of using the same;" US 2010-0226983 for "Compositions for treatment and prevention of acne, methods of making the compositions, and methods of use thereof;" US 2012-0171249 for "Compositions for inactivating pathogenic microorganisms, methods of making the compositions, and methods of use thereof;" and US 2012-0064136 for "Anti-aging and wrinkle treatment methods using nanoemulsion compositions." However, none of these references teach the methods, compositions and kits of the present invention.

In particular, U.S. Pat. No. 7,314,624 describes nanoemulsion vaccines. However, this reference does not teach the ability to induce a protective immune response to HSV using the immunogens of the invention.

Prior art directed to vaccines includes, for example, U.S. Pat. No. 7,731,967 for "Composition for inducing immune response" (Novartis), which describes an antigen/adjuvant complex comprising at least two adjuvants. U.S. Pat. No. 7,357,936 for "Adjuvant systems and vaccines" (GSK) describes a combination of adjuvant and antigens. U.S. Pat. No. 7,323,182 for "Oil in water emulsion containing saponins" (GSK) describes a vaccine composition with an oil/water formulation. U.S. Pat. No. 6,867,000 for "Method of enhancing immune response to herpes" (Wyeth) describes a combination of viral antigens and cytokines (IL12). U.S. Pat. No. 6,692,752 for "Methods of treating human females susceptible to HSV infection" (GSK) describes a method of treating an HSV 1-/2-female human subject susceptible to herpes simplex virus (HSV) infection. The method comprises administering to the subject an effective amount of a vaccine formulation comprising an adjuvant and an antigen which is or is derived from the group consisting of HSV-1 glycoprotein D, HSV-2 glycoprotein D and an immunological fragment thereof. U.S. Pat. Nos. 6,623,739, 6,372,227, and 6,146,632, all for "Vaccines" (GSK), are directed to an immunogenic composition comprising an antigen and/or antigen composition and an adjuvant consisting of a metabolizable oil and alpha tocopherol in the form of an oil in water emulsion. U.S. Pat. No. 6,451,325 for "Adjuvant formulation comprising a submicron oil droplet emulsion" (Chiron) is directed to an adjuvant composition comprising a metabolizable oil, an emulsifying agent, and an antigenic substance, wherein the oil and emulsifying agent are present in the form of an oil-in-water emulsion. The adjuvant composition does not contain any polyoxypropylene-polyoxyethylene block copolymer; and the antigenic substance is not present in the internal phase of the adjuvant composition. U.S. Pat. No. 6,027,730 for "HSV gD and 3 deacylated monophosphoryl lipid A" (GSK) describes a vaccine formulation comprising a Herpes Simplex Virus glycoprotein D or an immunological fragment of the Herpes Simplex Virus glycoprotein D, 3 Deacylated monophosphoryl lipid A and a carrier. The carrier is alum or an oil in water emulsion. U.S. Pat. No. 5,747,039 for "Recombinant herpes simplex gB-gD vaccine" (Chiron) describes a method for immunizing a human against herpes simplex virus (HSV) infection comprising vaccinating the human with an adjuvant and a vaccine formulation consisting essentially of HSV polypeptides. The HSV polypeptides are immunogenic, glycosylated, and consist of: (i) a HSV glycoprotein B polypeptide or a HSV glycoprotein B polypeptide that has a deletion of all or a portion of the transmembrane anchor region; and (ii) a HSV glycoprotein D polypeptide or a HSV glycoprotein D polypeptide that has a deletion of all or a portion of the transmembrane anchor region. U.S. Pat. No. 5,648,079 for "HSV gB Vaccine" (Chiron) describes a vaccine composition comprising a recombinantly produced glycosylated glycoprotein B (gB) polypeptide of Herpes Simplex Virus (HSV) that has a deletion of all or a portion of the transmembrane anchor region, in combination with a pharmacologically acceptable carrier and an adjuvant. U.S. Pat. No. 5,612,041 for "Recombinant HSV gD vaccine" (Chiron) describes a method for alleviating recurrent Herpes Simplex Virus (HSV) infection in a human comprising vaccinating the human subsequent to HSV infection with a vaccine consisting essentially of an adjuvant and a protein selected from the group consisting of glycoprotein D (gD) of HSV and a C-terminally truncated form of HSV gD which lacks all or a portion of the anchor sequence coding region. U.S. Pat. No. 5,171,568 for "Recombinant HSV gB-gD vaccine" (Chiron) describes a vaccine formulation consisting essentially of herpes simplex virus (HSV) polypeptides wherein the HSV polypeptides are immunogenic, glycosylated, and consist of: (i) a HSV glycoprotein B polypeptide or immunogenic fragments thereof; and (ii) a HSV glycoprotein D polypeptide or immunogenic fragments thereof. US 20110177125 for "HSV combined subunit vaccines and methods of use thereof" (U Penn-Friedman) describes a vaccine comprising a recombinant HSV-2 gD protein or immunogenic fragment thereof, a recombinant HSV-2 gC protein fragment, and an adjuvant. The HSV-2 gC protein fragment comprises a C3b-binding domain thereof, a properdin interfering domain thereof, a C5 interfering domain thereof or a fragment of the C3b-binding domain, properdin interfering domain, or C5-interfering domain. Finally, US 20040151734 for "Vaccine and method of use" (GSK) describes a method of treating a female human subject suffering from or susceptible to one or more sexually transmitted diseases (STDs). The method comprises administering to a female subject in need thereof an effective amount of a vaccine formulation comprising one or more antigens derived from or associated with an STD-causing pathogen and an adjuvant.

There remains a need in the art for an effective HSV vaccine and methods of making and using the same. The present invention satisfies these needs.

SUMMARY OF THE INVENTION

The present invention provides a novel approach for inducing a protective immune response against HSV infection. The vaccine can be useful against both HSV-1 and HSV-2 (throughout the application, "HSV" is used to collectively refer to HSV-1 and HSV-2). Combining a nanoemulsion with whole HSV virus (native or mutant) and/or multiple HSV surface antigens presents a novel combination that provides for the rational basis of vaccine development for use in humans. In one embodiment of the invention, the present invention provides compositions, methods and kits for inducing an immune response to HSV in a subject. Preferably, the vaccine compositions of the invention are capable of inducing Th1, Th2 and Th17 immune responses.

In one embodiment of the invention, encompassed is a vaccine composition comprising an immune enhancing nanoemulsion and whole HSV virus, either native or mutant, wherein the nanoemulsion further comprises an oil-in-water nanoemulsion or a dilution thereof, and wherein the HSV virus is preferably present within the nanoemulsion.

In another embodiment of the invention, encompassed is a vaccine composition comprising an immune enhancing nanoemulsion and at least one herpes simplex virus (HSV) surface antigen, wherein the nanoemulsion further comprises an oil-in-water nanoemulsion or a dilution thereof, and wherein the HSV antigens are preferably present within the nanoemulsion. For example, the HSV surface antigens can be derived from HSV and comprise at least one isolated HSV gB, gC, gD or gE glycoprotein or an immunogenic fragment thereof. In addition, one or more HSV surface antigens can further comprise nucleotide modifications denoting attenuating phenotypes. At least one HSV surface antigen can also be present in a fusion protein. For example, at least one HSV surface antigen can be present in an immunogenic peptide fragment of HSV gB, gC, gD or gE glycoprotein or a derivative thereof.

The HSV vaccine of the invention can comprise whole HSV virus combined with one or more HSV surface antigens.

In one embodiment encompassed by the invention is a vaccine composition comprising (1) at least one HSV immunogen (e.g., whole HSV virus or an isolated HSV surface antigen), (2) an aqueous phase, (3) at least one oil, (4) at least one surfactant, (5) at least one organic solvent, and (6) optionally at least one chelating agent. In yet another embodiment of the invention, the nanoemulsion HSV vaccine lacks an organic solvent. Furthermore, additional adjuvants may be added to the nanoemulsion HSV vaccine. The HSV immunogen is preferably a combination of at least two isolated surface glycoproteins from herpes simplex viruses, such as gB, gC, gD and gE glycoproteins, fusion proteins or fragments thereof. Alternatively, the HSV immunogen can be whole HSV virus, either native or mutant.

In another embodiment, encompassed by the invention is a subunit vaccine composition comprising an immune enhancing nanoemulsion combined with multivalent herpes simplex virus (HSV) surface antigens, wherein the nanoemulsion further comprises an oil-in-water nanoemulsion or dilution thereof and isolated viral antigens preferentially contained within the nanoemulsion. In particular, the multivalent surface antigens can be derived from HSV and comprise isolated HSV gB, gC, gD or gE glycoprotein or an immunogenic fragment thereof.

The vaccine compositions of the invention can, for example, have a nanoemulsion particle size of from about 300 nm up to about 600 nm. Other nanoemulsion particle sizes are also encompassed by the invention, such as a particle size of less than 1000 nm.

In addition, the vaccine compositions of the invention can further comprise an adjuvant and/or one or more pharmaceutically acceptable carriers.

The nanoemulsion HSV vaccine may be formulated in any pharmaceutically acceptable dosage form, such as a liquid dispersion, gel, aerosol, pulmonary aerosol, nasal aerosol, ointment, cream, or solid dose. In addition, the vaccine compositions of the invention can be administered via any pharmaceutically acceptable method. For example, the vaccine compositions of the invention can be administered either parenterally, orally, intravaginally, or intranasally. In addition, the parenteral administration can be by subcutaneous, intraperitoneal or intramuscular injection.

The methods of the invention comprise inducing an enhanced immunity against diseases caused by herpes simplex viruses comprising the step of administering to a subject an effective amount of a nanoemulsion HSV vaccine according to the invention. In particular, the methods of the invention comprise administering to a subject a nanoemulsion HSV vaccine comprising a nanoemulsion, wherein the nanoemulsion further comprises an oil-in-water nanoemulsion or a dilution thereof, and HSV whole virus (native or mutant), and/or at least one herpes simplex virus (HSV) surface antigen, wherein the HSV whole virus and/or one or more HSV antigens are present within the nanoemulsion.

In yet another embodiment of the invention, the nanoemulsion HSV vaccines of the invention are useful in treating and/or preventing an HSV infection which is drug resistant. For example the infection can be of an HSV strain resistant to an antiviral drug such as acyclovir.

In another embodiment of the invention, encompassed is a method for preparing a vaccine for the treatment or prevention of HSV infection in humans. The method can comprise synthesizing one or more HSV antigens in a eukaryotic host utilizing recombinant DNA genetics vectors and constructs, isolating the one or more surface antigens from the eukaryotic host, and formulating the surface antigens with an oil-in-water nanoemulsion to form a nanoemulsion HSV vaccine. The method can comprise synthesizing in a eukaryotic host a full length or fragment HSV surface antigen, and the antigen can be, for example, HSV gB, HSV gC, HSV gD, and/or HSV gE. The eukaryotic host can be, for example, a mammalian cell or a yeast cell.

The foregoing general description and following description of the drawings and the detailed description are exemplary and explanatory and are intended to provide further explanation of the invention as claimed. Other objects, advantages, and novel features will be readily apparent to those skilled in the art from the following detailed description of the invention.

DESCRIPTION OF THE FIGURES

FIG. 1: Shows TEM cross section images of the 20% $W_{80}5EC$ nanoemulsion with and without 30 µg total HA. FIG. 1A shows a 20% nanoemulsion without added antigen. FIG. 1B (panel on the right) shows a 20% nanoemulsion combined with 30 µg Fluzone®, and illustrates that the HA antigens are located in the oil droplets. The darkly stained antigens are located outside of the nanoemulsion particles.

DETAILED DESCRIPTION OF THE INVENTION

The present invention provides a novel approach for inducing a protective immune response against HSV infection. Combining a nanoemulsion with HSV whole virus and/or multiple HSV surface antigens presents a novel combination that provides for the rational basis of vaccine development for use in humans.

A. Definitions

The term "nanoemulsion," as used herein, includes small oil-in-water dispersions or droplets, as well as other lipid structures which can form as a result of hydrophobic forces which drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. The present invention contemplates that one skilled in the art will appreciate this distinction when necessary for understanding the specific embodiments herein disclosed. Nanoemulsion particle size generally varies from 300 to 600 nanometers.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the term "antigen" refers to proteins, glycoproteins or derivatives or fragment that can contain one or more epitopes (linear, conformation, sequential, T-cell) which can elicit an immune response. Antigens can be separated in isolated viral proteins or peptide derivatives.

As used herein, the term "isolated" refers to virus, proteins, glycoproteins, peptide derivatives or fragment or polynucleotide that is independent from its natural location. Viral components that are independently obtained through recombinant genetics means typically leads to products that are relatively purified.

As used herein, the term "adjuvant" refers to an agent that increases the immune response to an antigen (e.g., HSV surface antigens). As used herein, the term "immune response" refers to a subject's (e.g., a human or another animal) response by the immune system to immunogens (i.e., antigens) the subject's immune system recognizes as foreign. Immune responses include both cell-mediated immune responses (responses mediated by antigen-specific T cells and non-specific cells of the immune system—Th1, Th2, Th17) and humoral immune responses (responses mediated by antibodies). The term "immune response" encompasses both the initial "innate immune responses" to an immunogen (e.g., HSV surface antigens) as well as memory responses that are a result of "acquired immunity."

As used herein, the term "immune enhancing" refers to a significant boost in the level and breath of the innate and acquired immune response to a given pathogen following administration of a vaccine of the present invention relative to the level of innate and acquired immunity when a vaccine of the present invention has not been administered.

As used herein, the term "HSV whole virus" refers to native, recombinant, and mutant whole HSV virus, including HSV-1 and HSV-2.

As used herein, the term "HSV surface antigens" refers to proteins, glycoproteins and peptide fragments derived from the envelope of HSV-1 and HSV-2 viruses. Preferred HSV surface antigens are glycoproteins gB, gC, gD and gE derived from either HSV-1 or HSV-2. The HSV surface antigens are generally extracted from viral isolates from infected cell cultures, or produced by synthetically or using recombinant DNA methods. The HSV surface antigens can be modified by chemical, genetic or enzymatic means resulting in fusion proteins, peptides, or fragments.

As used herein, the term "gB" refers to HSV envelope glycoprotein B encoded by UL27 gene. The 110 kD glycoprotein contains multiple transmembrane segments and is essential for viral entry into host cells. As used herein, gB would encompass isolated mature glycoprotein, peptide fragments and fusion protein formed with gB and another peptide or protein component.

As used herein, the term "gC" refers to HSV envelope glycoprotein C encoded by UL44 gene. The HSV gC glycoprotein functions to mediate viral attachment to host cells and acts to modulate complement activation in the innate immune response. As used herein, gC would encompass isolated mature glycoprotein, peptide fragments and fusion protein formed with gC and another protein or peptide component.

As used herein, the term "gD" refers to HSV envelope glycoprotein encoded by US6 gene. The HSV gD glycoprotein is a multifunction protein with that helps to define viral host tropism. As used herein, gD would encompass isolated mature glycoprotein, peptide fragments and fusion protein formed with gD and another peptide and protein component.

As used herein, the term "gE" refers to HSV envelops glycoprotein encoded by US8 gene. The HSV gE glycoprotein has been shown to form a heterodimer with gl and functions in virion transport and modulating host defense. As used herein, gE would encompass isolated mature glycoprotein, peptide fragments, and fusion protein formed with gE and another peptide and protein component.

As used herein, the term "inactivated" HSV refers to virion particles that are incapable of infecting host cells and are noninfectious in pertinent animal models.

As used herein, the term "multivalent vaccines" refers to a vaccine comprising more than one antigenic determinant of a single viral agent or multiples strains. As used herein, multivalent vaccine comprise HSV whole virus and/or multiple HSV viral surface antigens, including viral glycoproteins gB, gC, gC and gE. Multivalent vaccines can be constructed with antigens derived from both HSV-1 and HSV-2.

As used herein, the term "subunit" refers to isolated and generally purified HSV glycoproteins that are individually or mixed further with nanoemulsion comprising a vaccine composition. The subunit vaccine composition is free from mature virions, cells or lysate of cell or virions. The method of obtaining a viral surface antigen that is included in a subunit vaccine can be conducted using standard recombinant genetics techniques and synthetic methods and with standard purification protocols.

B. General Description of the Invention

The present invention provides composition and methods for enhancement of the immune responses to HSV viruses. Specifically, the present invention provides composition and methods for the use of a nanoemulsion as an immune enhancer and adjuvant to boost and increase the breath of the immune response to HSV whole virus and/or surface antigens. In some embodiments, at least one isolated HSV surface antigen, from the list of gB, gC, gD and/or gE, are mixed in varied proportions with a nanoemulsion.

Prior to the present invention, it was observed that the novel broad-based immune enhancement functions of a nanoemulsion results in activation of multiple arms of the immune response to other viral pathogens and antigens, including influenza, hepatitis B surface antigens and respiratory syncytial virus. However, unlike influenza and hepatitis B virus, for which current licensed vaccines exist for human use, no current vaccines exist for HSV. In addition, multiple studies have shown that usage of traditional adjuvants with HSV surface antigens were not sufficient for an efficacious vaccine in humans (Bernstein et al., 2011; Corey et al., 1999; Dasgupta et al., 2011; Ashley et al., 1985).

The present invention is based on a novel combination of HSV whole virus and/or HSV surface antigens combined with a nanoemulsion and is contemplated to provide a robust and comprehensive immune response by inducing Th1, Th2 and Th17 arms of the immune response, which will result in a optimal prophylactic vaccine against HSV.

Experiments conducted with influenza and hepatitis B virus (HBV) demonstrated that a nanoemulsion coupled with a single viral antigen is capable of inducing a protective immune response (Makidon et al., 2008; Hamouda et al., 2010).

The present invention provides for the novel formulation of whole HSV virus and/or multiple HSV surface antigens in combination with a nanoemulsion to address the inadequate immune response observed in previous human clinical trials of HSV vaccines. An optimal vaccine against HSV would not only prevent against acute viral infection but also prevent against latency and reduce viral reactivation, which provides a source for recurrent and secondary infections.

Experiments conducted during the course of the development of the current invention demonstrated that a nanoemulsion added to hepatitis B surface antigen (HBsAg) and administered intranasally was a safe and effective hepatitis B vaccine. The mucosal vaccine induced a Th1 associated cellular immune response, with concomitant neutralizing antibodies production. A single nasal immunization of the HBsAg nanoemulsion mixture produced a rapid induction of serum antibodies that was comparable to currently administered intramuscular vaccines. Further, there was demonstration of affinity maturation in the antibody response, which is predictive of the potential efficacy of vaccine (Makidon et al., 2008).

Another emerging component of vaccine protective efficacy is the induction of T-helper-17 (Th17) cytokine responses. The demonstration that IL-17 contributes to the normal immune response to pathogens has been further utilized to show relevance in vaccination strategies (DeLyrica et al., 2009; Conti et al., 2009). In the development of the current invention, mucosal immunization with nanoemulsion can produce adjuvant effects in activating Th1 and Th17 immunity. Mucosal immunization with nanoemulsion resulted in activation of innate immune response which directly helps in the induction of Th1 and Th17 cells. The results further clarify the immune enhancing features of nanoemulsion importance in the field of vaccination for the induction of cellular immunity against pathogens, such as herpes simplex viruses (Bielinska et al., 2010)

The present invention provides compositions and methods for enhancement of the immune responses. Specifically, the present invention discloses compositions and methods for the use of nanoemulsions as an immune enhancer, providing adjuvant effects to HSV vaccine compositions.

In one embodiment of the invention, encompassed is a vaccine composition comprising an immune enhancing nanoemulsion and whole HSV virus, either native, recombinant, or mutant, wherein the nanoemulsion further comprises an oil-in-water nanoemulsion or a dilution thereof, and wherein the HSV virus is preferably present within the nanoemulsion.

In another embodiment, subunit vaccines can be constructed with one or more of HSV surface antigens mixed with nanoemulsion. It is entirely possible to have all four surface antigens, gB, gC, gD and gE added together and mixed with nanoemulsion in a resulting vaccine composition, as well as HSV whole virus. In another embodiment, one can have either gB, or gD or a combination of the antigens mixed with nanoemulsion for a proposed vaccine, as well as HSV whole virus. It is envisaged that any combination of HSV surface antigens, as well as HSV whole virus, can be mixed with nanoemulsion to produce a resulting vaccine composition. The vaccine composition can be delivered via intranasal, intravaginal, or other pharmaceutically acceptable route, including other mucosal routes.

In one embodiment, a multivalent subunit vaccine can be constructed utilizing surface glycoproteins, such as gB, gC, gD and gE derived from HSV-1 and HSV-2, and/or HSV whole virus, mixed with nanoemulsion. The antigens can be combined in various combinations to produce an effective vaccine against both types of herpes viruses.

The HSV vaccine of the invention can comprise whole HSV virus combined with one or more HSV surface antigens. In some embodiments, the present invention provides for a composition comprising HSV surface antigens and a nanoemulsion.

In one embodiment of the invention, the nanoemulsion HSV vaccine comprises at least one HSV immunogen (HSV whole virus and/or isolated HSV surface antigens) and droplets having an average diameter of less than about 1000 nm and: (a) an aqueous phase; (b) about 1% oil to about 80% oil; (c) about 0.1% to about 50% organic solvent; (d) about 0.001% to about 10% of a surfactant or detergent; or (e) any combination thereof. In another embodiment of the invention, the nanoemulsion vaccine comprises at least one HSV immunogen (HSV whole virus and/or isolated HSV surface antigens) and: (a) an aqueous phase; (b) about 1% oil to about 80% oil; (c) about 0.1% to about 50% organic solvent; (d) about 0.001% to about 10% of a surfactant or detergent; and (e) at least one HSV immunogen. In another embodiment of the invention, the nanoemulsion lacks an organic solvent.

The quantities of each component present in the nanoemulsion and/or nanoemulsion vaccine refer to a therapeutic nanoemulsion and/or nanoemulsion HSV vaccine.

In still a further embodiments, the nanoemulsion further comprises a quaternary ammonium-containing compound. The present invention is not limited to a particular quaternary ammonium containing compound. A variety of quaternary ammonium containing compounds are contemplated including, but not limited to, Alkyl dimethyl benzyl ammonium chloride, dialkyl dimethyl ammonium chloride, n-Alkyl dimethyl benzyl ammonium chloride, n-Alkyl dimethyl ethylbenzyl ammonium chloride, Dialkyl dimethyl ammonium chloride, and n-Alkyl dimethyl benzyl ammonium chloride.

In certain embodiments, the nanoemulsion further comprises a cationic halogen containing compound. The present invention is not limited to a particular cationic halogen containing compound. A variety of cationic halogen containing compounds are contemplated including, but not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, and tetradecyltrimethylammonium halides. The present invention nanoemulsion is also not limited to a particular halide. A variety of halides are contemplated including, but not limited to, halide selected from the group consisting of chloride, fluoride, bromide, and iodide.

The nanoemulsion HSV vaccine of the invention can be administered to a subject using any pharmaceutically acceptable method, such as for example, intranasal, buccal, sublingual, oral, rectal, ocular, parenteral (intravenously, intradermally, intramuscularly, subcutaneously, intracisternally, intraperitoneally), pulmonary, intravaginal, locally administered, topically administered, topically administered after scarification, mucosally administered, via an aerosol, or via a buccal or nasal spray formulation.

In yet another embodiment of the invention, the nanoemulsion HSV vaccines of the invention are useful in treating and/or preventing an HSV infection which is drug resistant. For example the infection can be of an HSV strain resistant to an antiviral drug such as acyclovir. The emergence of virus strains resistant to commonly used anti-herpesvirus drugs is a problem in the clinical setting, particularly in immunocompromised patients. The present invention satisfies this problem present in the prior art. HSV develops resistance predominantly as a result of mutations in genes that code for thymidine kinase (TK), but resistance can also result from mutations in DNA polymerase.

Further, the nanoemulsion HSV vaccine can be formulated into any pharmaceutically acceptable dosage form, such as a liquid dispersion, gel, aerosol, pulmonary aerosol, nasal aerosol, ointment, cream, semi-solid dosage form, or a suspension. Additionally, the nanoemulsion HSV vaccine may be a controlled release formulation, sustained release formulation, immediate release formulation, or any combination thereof. Further, the nanoemulsion HSV vaccine may be a transdermal delivery system such as a patch or administered by a pressurized or pneumatic device (i.e., a "gene gun").

The immune response of the subject can be measured by determining the titer and/or presence of antibodies against the HSV immunogen (e.g., HSV whole virus and/or an HSV surface antigen) after administration of the nanoemulsion HSV vaccine to evaluate the humoral response to the immunogen. Seroconversion refers to the development of specific antibodies to an immunogen and may be used to evaluate the presence of a protective immune response. Such antibody-based detection is often measured using Western blotting or enzyme-linked immunosorbent (ELISA) assays or hemagglutination inhibition assays (HAI). Persons of skill in the art would readily select and use appropriate detection methods.

Another method for determining the subject's immune response is to determine the cellular immune response, such as through immunogen-specific cell responses, such as cytotoxic T lymphocytes, or immunogen-specific lymphocyte proliferation assay. Additionally, challenge by the pathogen may be used to determine the immune response, either in the subject, or, more likely, in an animal model. A person of skill in the art would be well versed in the methods of determining the immune response of a subject and the invention is not limited to any particular method.

In another embodiment of the invention, the HSV vaccines of the invention result in generation of robust neutralizing antibodies. For example, administration of one or two doses of an HSV vaccine according to the invention can result in neutralizing antibody titers ranging from 2 to $10^6$ or more.

1. Virus Inactivation

Vaccines need to comprise inactivated virus, particularly when the vaccine comprises whole virus, e.g., to ensure that the vaccine does not cause the disease it is treating and/or preventing. In other words, inactivation of virus ensures that the vaccine does not comprise infectious particles. Approaches have included inactivation of viruses with formalin. However, formalin-inactivated vaccines have shown disease-enhancement, including showing a skewed immune response that is important to prevent disease-enhancement, and priming by mature dendritic cells, which are essential for a protective immune response. The use of live attenuated vaccines has met with limited success, as the vaccines have been shown to be minimally immunogenic.

In the methods and compositions of the invention, the nanoemulsion functions to inactivate and adjuvante the whole virus and/or viral antigens to provide a non-infectious and immunogenic virus. Alternatively, the virus (whole or antigens) can be inactivated prior to combining with the nanoemulsion. Examples of chemical methods of viral inactivation include, but are not limited to, formalin or β-propiolactone (β-PL), physical methods of viral inactivation include using heat or irradiation, or by molecular genetics means to produce a non-infectious particles. The simple mixing of a nanoemulsion with a vaccine candidate has been shown to produce both mucosal and system immune response. The mixing of the HSV virion particles with a nanoemulsion results in discrete antigen particles in the oil core of the droplet. The antigen is incorporated within the core and this allows it to be in a free form which promotes the normal antigen conformation.

C. Nanoemulsion HSV Vaccines

1. HSV Immunogen

The HSV immunogen present in the nanoemulsion HSV vaccines of the invention can be whole HSV virus (HSV-1 or HSV-2), including native, recombinant, and mutant strains of HSV-1 and HSV-2. In one embodiment of the invention, the HSV virus can be resistant to one or more antiviral drugs, such as resistant to acyclovir. Any known HSV strain can be used in the vaccines of the invention.

Examples of useful strains of HSV include, but are not limited to, HSV strain deposited with the ATCC, such as: (1) HSV Strain HF (ATCC VR-260; Human herpesvirus 1); (2) HSV Strain MacIntyre (ATCC VR-539; Human herpesvirus 1); (3) HSV Strain MS (ATCC VR-540; Human herpesvirus 2); (4) HSV Strain F (ATCC VR-733; Human herpesvirus 1); (5) HSV Strain G (ATCC VR-734; Human herpesvirus 2); (6) HSV Strain MP (ATCC VR-735; Human herpesvirus 1, mutant strain of herpes simplex virus type 1); (7) Mutant Strain of HSV (ATCC VR-1383; Human herpesvirus 1, mutant strain of herpes simplex virus type 1); (8) HSV Stain KOS (ATCC VR-1493; Human herpesvirus 1; derived from ATCC VR-1487 by passage in the presence of MRA to remove mycoplasma contaminants); (9) HSV Strain ATCC-2011-1 (ATCC VR-1778; Human herpesvirus 1); (10) HSV Strain ATCC-2011-2 (ATCC VR-1779; Human herpesvirus 2); (11) HSV Strain ATCC-2011-4 (ATCC VR-1781; Human herpesvirus 2); (12) HSV Strain A5C (ATCC VR-2019; Human herpesvirus 1×2 (recombinant); Source: Crossing of parental strains of HSV-1 (17ts) and HSV-2 (GPG)); (13) HSV Strain D4E3 (ATCC VR-2021; Human herpesvirus 1×2 (recombinant); Source: Crossing of parental strains of HSV-1 (KOStsE6) and HSV-2 (186tsB5)); (14) HSV Strain C7D (ATCC VR-2022; Human herpesvirus 1×2 (recombinant); Source: Crossing of parental strains of HSV-1 (HFEMtsN102) and HSV-2 (186)); (15) HSV Strain D3E2 (ATCC VR-2023; Human herpesvirus 1×2 (recombinant); Source: Crossing of parental strains of HSV-1 (KOStsE6) and HSV-2 (186tsB5)); (16) HSV Strain C5D (ATCC VR-2024; Human herpesvirus 1×2 (recombinant); Source: Crossing of parental strains of HSV-1 (HFEMtsN102) and HSV-2 (186); (17) HSV Strain D5E1 (ATCC VR-2025; Human herpesvirus 1×2 (recombinant); Source: Crossing of parental strains of HSV-1 (KOStsE6) and HSV-2 (186tsB5); and (18) HSV Strain D1E1 (ATCC VR-2026; Human herpesvirus 1×2 (recombinant); Source: Crossing of parental strains of HSV-1 (KOStsE6) and HSV-2 (186tsB5)).

Additionally, the HSV immunogen present in the nanoemulsion HSV vaccines of the invention can be one or more HSV surface antigens, which are proteins, glycoproteins and peptide fragments derived from the envelope of HSV-1 and HSV-2 viruses. Preferred HSV surface antigens are glycoproteins gB, gC, gD and gE derived from either HSV-1 or HSV-2. The HSV surface antigens are generally extracted from viral isolates from infected cell cultures, or produced by synthetically or using recombinant DNA methods. The HSV surface antigens can be modified by chemical, genetic or enzymatic means resulting in fusion proteins, peptides, or fragments. The HSV surface antigens can be obtained from any known HSV strain, including but not limited to the strains listed above.

The HSV immunogen present in the vaccines of the invention can also be whole HSV virus combined with one or more HSV surface antigens.

Any suitable amount of HSV immunogen can be used in the nanoemulsion HSV vaccines of the invention. For example, the nanoemulsion HSV vaccine can comprise less than about 100 µg of HSV immunogen (total HSV immunogen and not per HSV immunogen). In another embodiment of the invention, the nanoemulsion HSV vaccine can comprise less than about 90 µg, less than about 80 µg, less than about 70 µg, less than about 60 µg, less than about 50 µg, less than about 40 µg, less than about 30 µg, less than about 20 µg, less than about 15 µg, less than about 10 µg, less than about 9 µg, less than about 8 µg, less than about 7 µg, less than about 6 µg, less than about 5 µg, less than about 4 µg, less than about 3 µg, less than about 2 µg, or less than about 1 µg of HSV immunogen (total HSV immunogen and not per HSV immunogen).

In another embodiment of the invention, the HSV vaccines of the invention comprise about $1.0 \times 10^5$ pfu (plaque forming units (pfu) up to about $1.0 \times 10^8$ pfu, and any amount in-between, of an HSV virus or antigen. The HSV virus or antigen is inactivated by the presence of the nanoemulsion adjuvant. For example, the HSV vaccines can comprise about $1.0 \times 10^5$, $1.1 \times 10^5$, $1.2 \times 10^5$, $1.3 \times 10^5$, $1.4 \times 10^5$, $1.5 \times 10^5$, $1.6 \times 10^5$, $1.7 \times 10^5$, $1.8 \times 10^5$, $1.9 \times 10^5$, $2.0 \times 10^5$, $2.1 \times 10^5$, $2.2 \times 10^5$, $2.3 \times 10^5$, $2.4 \times 10^5$, $2.5 \times 10^5$, $2.6 \times 10^5$, $2.7 \times 10^5$, $2.8 \times 10^5$, $2.9 \times 10^5$, $3.0 \times 10^5$, $3.1 \times 10^5$, $3.2 \times 10^5$, $3.3 \times 10^5$, $3.4 \times 10^5$, $3.5 \times 10^5$, $3.6 \times 10^5$, $3.7 \times 10^5$, $3.8 \times 10^5$, $3.9 \times 10^5$, $4.0 \times 10^5$, $4.1 \times 10^5$, $4.2 \times 10^5$, $4.3 \times 10^5$, $4.4 \times 10^5$, $4.5 \times 10^5$, $4.6 \times 10^5$, $4.7 \times 10^5$, $4.8 \times 10^5$, $4.9 \times 10^5$, $5.0 \times 10^5$, $5.5 \times 10^5$, $6.0 \times 10^5$, $6.5 \times 10^5$, $7.0 \times 10^5$, $7.5 \times 10^5$, $8.0 \times 10^5$, $8.5 \times 10^5$, $9.0 \times 10^5$, $9.5 \times 10^5$, $1.0 \times 10^6$, $1.5 \times 10^6$, $2.0 \times 10^6$, $2.5 \times 10^6$, $3.0 \times 10^6$, $3.5 \times 10^6$, $4.0 \times 10^6$, $4.5 \times 10^6$, $5.0 \times 10^6$, $5.5 \times 10^6$, $6.0 \times 10^6$, $6.5 \times 10^6$, $7.0 \times 10^6$, $7.5 \times 10^6$, $8.0 \times 10^6$, $8.5 \times 10^6$, $9.0 \times 10^6$, $9.5 \times 10^6$, $1.0 \times 10^7$, $1.5 \times 10^7$, $2.0 \times 10^7$, $2.5 \times 10^7$, $3.0 \times 10^7$, $3.5 \times 10^7$, $4.0 \times 10^7$, $4.5 \times 10^7$, $5.0 \times 10^7$, $5.5 \times 10^7$, $6.0 \times 10^7$, $6.5 \times 10^7$, $7.0 \times 10^7$, $7.5 \times 10^7$, $8.0 \times 10^7$, $8.5 \times 10^7$, $9.0 \times 10^7$, $9.5 \times 10^7$, $1.0 \times 10^8$ pfu of an HSV virus.

In another embodiment of the invention, the HSV vaccines of the invention are cross-reactive against at least one other HSV strain not present in the vaccine (or cross-reactive against one or more HSV strains). For example, a nanoemulsion HSV vaccine according to the invention can comprise HSV-1 virus or viral particles and be cross-reactive against HSV-2. As it is known to one of ordinary skill in the art, cross reactivity can be measured 1) using ELISA method to see if the sera from vaccinated animals or individuals will produce antibodies against strains that were not used in the administered vaccine; 2) Immune cells will produce cytokines when stimulated in vitro using stains that were not used in the administered vaccine. Cross protection can be measured in vitro when antibodies in sera of animals vaccinated with one strain will neutralize infectivity of another virus not used in the administered vaccine.

2. Nanoemulsion

As described above, a nanoemulsion to be combined with at least one HSV immunogen to make a nanoemulsion HSV vaccine according to the invention comprises an aqueous phase, at least one solvent, at least one oil, and at least one surfactant.

i. Aqueous Phase

The aqueous phase can comprise any type of aqueous phase including, but not limited to, water (e.g., $H_2O$, distilled water, purified water, water for injection, deionized water, tap water) and solutions (e.g., phosphate buffered saline (PBS) solution). In certain embodiments, the aqueous phase comprises water at a pH of about 4 to 10, preferably about 6 to 8. The water can be deionized (hereinafter "$DiH_2O$"). In some embodiments the aqueous phase comprises phosphate buffered saline (PBS). The aqueous phase may further be sterile and pyrogen free.

ii. Solvents

The present invention nanoemulsion is also not limited to a particular solvent, such as an organic solvent. A variety of solvents are contemplated including, but not limited to, an alcohol (e.g., including, but not limited to, methanol, ethanol, propanol, and octanol), glycerol, polyethylene glycol, and an organic phosphate based solvent.

Organic solvents in the nanoemulsion HSV vaccines of the invention include, but are not limited to, $C_1$-$C_{12}$ alcohol, diol, triol, dialkyl phosphate, tri-alkyl phosphate, such as tri-n-butyl phosphate, semi-synthetic derivatives thereof, and combinations thereof. In one aspect of the invention, the organic solvent is an alcohol chosen from a nonpolar solvent, a polar solvent, a protic solvent, or an aprotic solvent.

Suitable organic solvents for the nanoemulsion HSV vaccine include, but are not limited to, ethanol, methanol, isopropyl alcohol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, glycerol, sorbitol, industrial methylated spirit, triacetin, hexane, benzene, toluene, diethyl ether, chloroform, 1,4-dixoane, tetrahydrofuran, dichloromethane, acetone, acetonitrile, dimethylformamide, dimethyl sulfoxide, formic acid, semi-synthetic derivatives thereof, and any combination thereof.

iii. Oil Phase

The oil in the nanoemulsion HSV vaccine of the invention can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

The present invention nanoemulsion is not limited to particular oil. A variety of oils are contemplated, including, but not limited to, soybean, avocado, squalene, olive, canola, corn, rapeseed, safflower, sunflower, fish, flavor, and water insoluble vitamins. Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, $C_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (simmondsia chinensis seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, chenopodium oil, citronellal, citral, citronellol, chamazulene, yarrow, guaiazulene, chamomile, semi-synthetic derivatives, or combinations thereof.

In one aspect of the invention, the volatile oil in the silicone component is different than the oil in the oil phase.

iv. Surfactants

In some embodiments, the nanoemulsion further comprises a surfactant. The present invention is not limited to a particular surfactant. A variety of surfactants are contemplated including, but not limited to, nonionic and ionic surfactants (e.g., TRITON X-100; TWEEN 20; and TYLOXAPOL).

The surfactant in the nanoemulsion HSV vaccine of the invention can be a pharmaceutically acceptable ionic surfactant, a pharmaceutically acceptable nonionic surfactant, a pharmaceutically acceptable cationic surfactant, a pharmaceutically acceptable anionic surfactant, a pharmaceutically acceptable zwitterionic surfactant, or any combination thereof.

In one embodiment, the nanoemulsion HSV vaccine comprises a cationic surfactant which is cetylpyridinium chloride (CPC). CPC may have a concentration in the nanoemulsion HSV vaccine of less than about 5.0% and greater than about 0.001%, or further, may have a concentration of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, less than about 0.10%, greater than about 0.001%, greater than about 0.002%, greater than about 0.003%, greater than about 0.004%, greater than about 0.005%, greater than about 0.006%, greater than about 0.007%, greater than about 0.008%, greater than about 0.009%, or greater than about 0.010%.

In a further embodiment, the nanoemulsion HSV vaccine comprises a non-ionic surfactant, such as a polysorbate surfactant, which may be polysorbate 80 or polysorbate 20, and may have a concentration of about 0.01% to about 5.0%, or about 0.1% to about 3% of polysorbate 80. The nanoemulsion HSV vaccine may further comprise at least one preservative. In another embodiment of the invention, the nanoemulsion HSV vaccine comprises a chelating agent.

Exemplary useful surfactants are described in Applied Surfactants: Principles and Applications. Tharwat F. Tadros, Copyright 8 2005 WILEY-VCH Verlag GmbH & Co. KGaA, Weinheim ISBN: 3-527-30629-3), which is specifically incorporated by reference.

Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a non-polar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxysterate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thighlycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or distearate, polyoxyethylene fatty ethers, Polyoxyethylene lauryl ether, Polyoxyethylene stearyl ether, polyoxyethylene myristyl ether, a steroid, Cholesterol, Betasitosterol, Bisabolol, fatty acid esters of alcohols, isopropyl myristate, Aliphati-isopropyl n-butyrate, Isopropyl n-hexanoate, Isopropyl n-decanoate, Isoproppyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5$—$(OCH_2\ CH_2)_y$—OH, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23.

In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis[imidazoyl carbonyl]), nonoxynol-9, Bis(polyethylene glycol bis[imidazoyl carbonyl]), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quarternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl (tetradecyl)ammonium bromide, 1,3,5-Triazine-1,3,5(2H,4H,6H)-triethanol, 1-Decanaminium, N-decyl-N,N-dimethyl-, chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy)ethoxy) ethyl dimethyl benzyl ammonium chloride, Alkyl 1 or 3 benzyl-1-(2-hydroxethyl)-2-imidazolinium chloride, Alkyl bis(2-hydroxyethyl)benzyl ammonium chloride, Alkyl demethyl benzyl ammonium chloride, Alkyl dimethyl 3,4-dichlorobenzyl ammonium chloride (100% $C_{12}$), Alkyl dimethyl 3,4-dichlorobenzyl ammonium chloride (50% $C_{14}$, 40% $C_{12}$, 10% $C_{16}$), Alkyl dimethyl 3,4-dichlorobenzyl ammonium chloride (55% $C_{14}$, 23% $C_{12}$, 20% $C_{16}$), Alkyl dimethyl benzyl ammonium chloride, Alkyl dimethyl benzyl ammonium chloride (100% $C_{14}$), Alkyl dimethyl benzyl ammonium chloride (100% $C_{16}$), Alkyl dimethyl benzyl ammonium chloride (41% $C_{14}$, 28% $C_{12}$), Alkyl dimethyl benzyl ammonium chloride (47% $C_{12}$, 18% $C_{14}$), Alkyl dimethyl benzyl ammonium chloride (55% $C_{16}$, 20% $C_{14}$), Alkyl dimethyl benzyl ammonium chloride (58% $C_{14}$, 28% $C_{16}$), Alkyl dimethyl benzyl ammonium chloride (60% $C_{14}$, 25% $C_{12}$), Alkyl dimethyl benzyl ammonium chloride (61% $C_{ii}$, 23% $C_{14}$), Alkyl dimethyl benzyl ammonium chloride (61% $C_{12}$, 23% $C_{14}$), Alkyl dimethyl benzyl ammonium chloride (65% $C_{12}$, 25% $C_{14}$), Alkyl dimethyl benzyl ammonium chloride (67% $C_{12}$, 24% $C_{14}$), Alkyl dimethyl benzyl ammonium chloride (67% $C_{12}$, 25% $C_{14}$), Alkyl dimethyl benzyl ammonium chloride (90% $C_{14}$, 5% $C_{12}$), Alkyl dimethyl benzyl ammonium chloride (93% $C_{14}$, 4% $C_{12}$), Alkyl dimethyl benzyl ammonium chloride (95% $C_{16}$, 5% $C_{18}$), Alkyl dimethyl benzyl ammonium chloride, Alkyl didecyl dimethyl ammonium chloride, Alkyl dimethyl benzyl ammonium chloride, Alkyl dimethyl benzyl ammonium chloride ($C_{12-14}$ Alkyl dimethyl benzyl ammonium chloride ($C_{12-18}$), Alkyl dimethyl benzyl ammonium chloride, dialkyl dimethyl benzyl ammonium chloride, Alkyl dimethyl dimethybenzyl ammonium chloride, Alkyl dimethyl ethyl ammonium bromide (90% $C_{14}$, 5% $C_{16}$, 5% $C_{12}$), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% $C_{14}$), Alkyl dimethyl isopropylbenzyl ammonium chloride (50% $C_{12}$, 30% $C_{14}$, 17% $C_{16}$, 3% $C_{18}$), Alkyl trimethyl ammonium chloride (58% $C_{18}$, 40% $C_{16}$, 1% $C_{14}$, 1% $C_{12}$), Alkyl trimethyl ammonium chloride (90% $C_{18}$, 10% $C_{16}$), Alkyldimethyl (ethylbenzyl) ammonium chloride ($C_{12-18}$), Di-($C_{8-10}$)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis(2-hydroxyethyl) octyl hydrogen ammonium chloride, Dodecyl dimethyl benzyl ammonium chloride, Dodecylcarbamoyl methyl dimethyl benzyl ammonium chloride, Heptadecyl hydroxyethylimidazolinium chloride, Hexahydro-1,3,5-tris(2-hydroxyethyl)-s-triazine, Hexahydro-1,3,5-tris(2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysily propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present invention are not limited to formulation with an particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4, 1-Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, Trizma® dodecyl sulfate, TWEEN® 80, Ursodeoxycholic acid, semi-synthetic derivatives thereof, and combinations thereof.

Suitable zwitterionic surfactants include, but are not limited to, an N-alkyl betaine, lauryl amindo propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio)propanesulfonate inner salt, 3-(Dodecyldimethylammonio)propanesulfonate inner salt, SigmaUltra, 3-(Dodecyldimethylammonio)propanesulfonate inner salt, 3-(N,N-Dimethylmyristylammonio)propanesulfonate, 3-(N,N-Dimethyloctadecylammonio)propanesulfonate, 3-(N,N-Dimethyloctylammonio) propanesulfonate inner salt, 3-(N,N-Dimethylpalmitylammonio)propanesulfonate, semi-synthetic derivatives thereof, and combinations thereof.

In some embodiments, the nanoemulsion HSV vaccine comprises a cationic surfactant, which can be cetylpyridinium chloride. In other embodiments of the invention, the nanoemulsion HSV vaccine comprises a cationic surfactant, and the concentration of the cationic surfactant is less than about 5.0% and greater than about 0.001%. In yet another embodiment of the invention, the nanoemulsion HSV vaccine comprises a cationic surfactant, and the concentration of the cationic surfactant is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, or less than about 0.10%. Further, the concentration of the cationic agent in the nanoemulsion vaccine is greater than about 0.002%, greater than about 0.003%, greater than about 0.004%, greater than about 0.005%, greater than about 0.006%, greater than about 0.007%, greater than about 0.008%, greater than about 0.009%, greater than about 0.010%, or greater than about 0.001%. In one embodiment, the concentration of the cationic agent in the nanoemulsion vaccine is less than about 5.0% and greater than about 0.001%.

In another embodiment of the invention, the nanoemulsion vaccine comprises at least one cationic surfactant and at least one non-cationic surfactant. The non-cationic surfactant is a nonionic surfactant, such as a polysorbate (Tween), such as polysorbate 80 or polysorbate 20. In one embodiment, the non-ionic surfactant is present in a concentration of about 0.01% to about 5.0%, or the non-ionic surfactant is present in a concentration of about 0.1°)/0 to about 3%. In yet another embodiment of the invention, the nanoemulsion vaccine comprises a cationic surfactant present in a concentration of about 0.01% to about 2%, in combination with a nonionic surfactant.

3. Additional Ingredients

Additional compounds suitable for use in the nanoemulsion HSV vaccines of the invention include but are not limited to one or more solvents, such as an organic phosphate-based solvent, bulking agents, coloring agents, pharmaceutically acceptable excipients, a preservative, pH adjuster, buffer, chelating agent, etc. The additional compounds can be admixed into a previously emulsified nanoemulsion vaccine, or the additional compounds can be added to the original mixture to be emulsified. In certain of these embodiments, one or more additional compounds are admixed into an existing nanoemulsion composition immediately prior to its use.

Suitable preservatives in the nanoemulsion HSV vaccines of the invention include, but are not limited to, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocophernol, ascorbic acid, ascorbyl palmitate, butylated hydroxyanisole, butylated hydroxytoluene, sodium ascorbate, sodium metabisulphite, citric acid, edetic acid, semi-synthetic derivatives thereof, and combinations thereof. Other suitable preservatives include, but are not limited to, benzyl alcohol, chlorhexidine (bis (p-chlorophenyldiguanido) hexane), chlorphenesin (3-(-4-chloropheoxy)-propane-1,2-diol), Kathon CG (methyl and methylchloroisothiazolinone), parabens (methyl, ethyl, propyl, butyl hydrobenzoates), phenoxyethanol (2-phenoxyethanol), sorbic acid (potassium sorbate, sorbic acid), Phenonip (phenoxyethanol, methyl, ethyl, butyl, propyl parabens), Phenoroc (phenoxyethanol 0.73%, methyl paraben 0.2%, propyl paraben 0.07%), Liquipar Oil (isopropyl, isobutyl, butylparabens), Liquipar PE (70% phenoxyethanol, 30% liquipar oil), Nipaguard MPA (benzyl alcohol (70%), methyl & propyl parabens), Nipaguard MPS (propylene glycol, methyl & propyl parabens), Nipasept (methyl, ethyl and propyl parabens), Nipastat (methyl, butyl, ethyl and propyel parabens), Elestab 388 (phenoxyethanol in propylene glycol plus chlorphenesin and methylparaben), and Killitol (7.5% chlorphenesin and 7.5% methyl parabens).

The nanoemulsion HSV vaccine may further comprise at least one pH adjuster. Suitable pH adjusters in the nanoemulsion vaccine of the invention include, but are not limited to, diethyanolamine, lactic acid, monoethanolamine, triethylanolamine, sodium hydroxide, sodium phosphate, semi-synthetic derivatives thereof, and combinations thereof.

In addition, the nanoemulsion HSV vaccine can comprise a chelating agent. In one embodiment of the invention, the chelating agent is present in an amount of about 0.0005% to about 1%. Examples of chelating agents include, but are not limited to, ethylenediamine, ethylenediaminetetraacetic acid (EDTA), phytic acid, polyphosphoric acid, citric acid, gluconic acid, acetic acid, lactic acid, and dimercaprol, and a preferred chelating agent is ethylenediaminetetraacetic acid.

The nanoemulsion HSV vaccine can comprise a buffering agent, such as a pharmaceutically acceptable buffering agent. Examples of buffering agents include, but are not limited to, 2-Amino-2-methyl-1,3-propanediol, ≥99.5% (NT), 2-Amino-2-methyl-1-propanol, ≥99.0% (GC), L-(+)-Tartaric acid, ≥99.5% (T), ACES, ≥99.5% (T), ADA, ≥99.0% (T), Acetic acid, ≥99.5% (GC/T), Acetic acid, for luminescence, ≥99.5% (GC/T), Ammonium acetate solution, for molecular biology, ~5 M in $H_2O$, Ammonium acetate, for luminescence, ≥99.0% (calc. on dry substance, T), Ammonium bicarbonate, ≥99.5% (T), Ammonium citrate dibasic, ≥99.0% (T), Ammonium formate solution, 10 M in $H_2O$, Ammonium formate, ≥99.0% (calc. based on dry substance, NT), Ammonium oxalate monohydrate, ≥99.5% (RT), Ammonium phosphate dibasic solution, 2.5 M in $H_2O$, Ammonium phosphate dibasic, ≥99.0% (T), Ammonium phosphate monobasic solution, 2.5 M in $H_2O$, Ammonium phosphate monobasic, ≥99.5% (T), Ammonium sodium phosphate dibasic tetrahydrate, ≥99.5% (NT), Ammonium sulfate solution, for molecular biology, 3.2 M in $H_2O$, Ammonium tartrate dibasic solution, 2 M in $H_2O$ (colorless solution at 20° C.), Ammonium tartrate dibasic, ≥99.5% (T), BES buffered saline, for molecular biology, 2× concentrate, BES, ≥99.5% (T), BES, for molecular biology, ≥99.5% (T), BICINE buffer Solution, for molecular biology, 1 M in $H_2O$, BICINE, ≥99.5% (T), BIS-TRIS, ≥99.0% (NT), Bicarbonate buffer solution, >0.1 M $Na_2CO_3$, >0.2 M $NaHCO_3$, Boric acid, ≥99.5% (T), Boric acid, for molecular biology, ≥99.5% (T), CAPS, ≥99.0% (TLC), CHES, 99.5% (T), Calcium acetate hydrate, ≥99.0% (calc. on dried material, KT), Calcium carbonate, precipitated, ≥99.0% (KT), Calcium citrate tribasic tetrahydrate, ≥98.0% (calc. on dry substance, KT), Citrate Concentrated Solution, for molecular biology, 1 M in $H_2O$, Citric acid, anhydrous, ≥99.5% (T), Citric acid, for luminescence, anhydrous, ≥99.5% (T), Diethanolamine, ≥99.5% (GC), EPPS, ≥99.0% (T), Ethylenediaminetetraacetic acid disodium salt dihydrate, for molecular biology, ≥99.0% (T), Formic acid solution, 1.0 M in H₂O, Gly-Gly-Gly, ≥99.0% (NT), Gly-Gly, ≥99.5% (NT), Glycine, ≥99.0% (NT), Glycine, for luminescence, ≥99.0% (NT), Glycine, for molecular biology, ≥99.0% (NT), HEPES buffered saline, for molecular biology, 2× concentrate, HEPES, ≥99.5% (T), HEPES, for molecular biology, 99.5% (T), Imidazole buffer Solution, 1 M in H₂O, Imidazole, ≥99.5% (GC), Imidazole, for luminescence, ≥99.5% (GC), Imidazole, for molecular biology, ≥99.5% (GC), Lipoprotein Refolding Buffer, Lithium acetate dihydrate, ≥99.0% (NT), Lithium citrate tribasic tetrahydrate, ≥99.5% (NT), MES hydrate, ≥99.5% (T), MES monohydrate, for luminescence, ≥99.5% (T), MES solution, for molecular biology, 0.5 M in H₂O, MOPS, ≥99.5% (T), MOPS, for luminescence, ≥99.5% (T), MOPS, for molecular biology, ≥99.5% (T), Magnesium acetate solution, for molecular biology, ~1 M in H₂O, Magnesium acetate tetrahydrate, ≥99.0% (KT), Magnesium citrate tribasic nonahydrate, ≥98.0% (calc. based on dry substance, KT), Magnesium formate solution, 0.5 M in H₂O, Magnesium phosphate dibasic trihydrate, ≥98.0% (KT), Neutralization solution for the in-situ hybridization for in-situ hybridization, for molecular biology, Oxalic acid dihydrate, ≥99.5% (RT), PIPES, ≥99.5% (T), PIPES, for molecular biology, ≥99.5% (T), Phosphate buffered saline, solution (autoclaved), Phosphate buffered saline, washing buffer for peroxidase conjugates in Western Blotting, 10× concentrate, piperazine, anhydrous, ≥99.0% (T), Potassium D-tartrate monobasic, ≥99.0% (T), Potassium acetate solution, for molecular biology, Potassium acetate solution, for molecular biology, 5 M in H₂O, Potassium acetate solution, for molecular biology, ~1 M in H₂O, Potassium acetate, ≥99.0% (NT), Potassium acetate, for luminescence, ≥99.0% (NT), Potassium acetate, for molecular biology, ≥99.0% (NT), Potassium bicarbonate, ≥99.5% (T), Potassium carbonate, anhydrous, ≥99.0% (T), Potassium chloride, ≥99.5% (AT), Potassium citrate monobasic, ≥99.0% (dried material, NT), Potassium citrate tribasic solution, 1 M in H₂O, Potassium formate solution, 14 M in H₂O, Potassium formate, ≥99.5% (NT), Potassium oxalate monohydrate, ≥99.0% (RT), Potassium phosphate dibasic, anhydrous, ≥99.0% (T), Potassium phosphate dibasic, for luminescence, anhydrous, ≥99.0% (T), Potassium phosphate dibasic, for molecular biology, anhydrous, ≥99.0% (T), Potassium phosphate monobasic, anhydrous, ≥99.5% (T), Potassium phosphate monobasic, for molecular biology, anhydrous, ≥99.5% (T), Potassium phosphate tribasic monohydrate, ≥95% (T), Potassium phthalate monobasic, ≥99.5% (T), Potassium sodium tartrate solution, 1.5 M in H₂O, Potassium sodium tartrate tetrahydrate, ≥99.5% (NT), Potassium tetraborate tetrahydrate, ≥99.0% (T), Potassium tetraoxalate dihydrate, ≥99.5% (RT), Propionic acid solution, 1.0 M in H₂O, STE buffer solution, for molecular biology, pH 7.8, STET buffer solution, for molecular biology, pH 8.0, Sodium 5,5-diethylbarbiturate, ≥99.5% (NT), Sodium acetate solution, for molecular biology, ~3 M in H₂O, Sodium acetate trihydrate, ≥99.5% (NT), Sodium acetate, anhydrous, ≥99.0% (NT), Sodium acetate, for luminescence, anhydrous, ≥99.0% (NT), Sodium acetate, for molecular biology, anhydrous, ≥99.0% (NT), Sodium bicarbonate, ≥99.5% (T), Sodium bitartrate monohydrate, ≥99.0% (T), Sodium carbonate decahydrate, ≥99.5% (T), Sodium carbonate, anhydrous, ≥99.5% (calc. on dry substance, T), Sodium citrate monobasic, anhydrous, ≥99.5% (T), Sodium citrate tribasic dihydrate, ≥99.0% (NT), Sodium citrate tribasic dihydrate, for luminescence, ≥99.0% (NT), Sodium citrate tribasic dihydrate, for molecular biology, ≥99.5% (NT), Sodium formate solution, 8 M in H₂O, Sodium oxalate, ≥99.5% (RT), Sodium phosphate dibasic dihydrate, ≥99.0% (T), Sodium phosphate dibasic dihydrate, for luminescence, ≥99.0% (T), Sodium phosphate dibasic dihydrate, for molecular biology, ≥99.0% (T), Sodium phosphate dibasic dodecahydrate, ≥99.0% (T), Sodium phosphate dibasic solution, 0.5 M in H₂O, Sodium phosphate dibasic, anhydrous, ≥99.5% (T), Sodium phosphate dibasic, for molecular biology, ≥99.5% (T), Sodium phosphate monobasic dihydrate, ≥99.0% (T), Sodium phosphate monobasic dihydrate, for molecular biology, ≥99.0% (T), Sodium phosphate monobasic monohydrate, for molecular biology, ≥99.5% (T), Sodium phosphate monobasic solution, 5 M in H₂O, Sodium pyrophosphate dibasic, ≥99.0% (T), Sodium pyrophosphate tetrabasic decahydrate, ≥99.5% (T), Sodium tartrate dibasic dihydrate, ≥99.0% (NT), Sodium tartrate dibasic solution, 1.5 M in H₂O (colorless solution at 20° C.), Sodium tetraborate decahydrate, ≥99.5% (T), TAPS, ≥99.5% (T), TES, ≥99.5% (calc. based on dry substance, T), TM buffer solution, for molecular biology, pH 7.4, TNT buffer solution, for molecular biology, pH 8.0, TRIS Glycine buffer solution, 10× concentrate, TRIS acetate-EDTA buffer solution, for molecular biology, TRIS buffered saline, 10× concentrate, TRIS glycine SDS buffer solution, for electrophoresis, 10× concentrate, TRIS phosphate-EDTA buffer solution, for molecular biology, concentrate, 10× concentrate, Tricine, ≥99.5% (NT), Triethanolamine, ≥99.5% (GC), Triethylamine, ≥99.5% (GC), Triethylammonium acetate buffer, volatile buffer, ~1.0 M in H₂O, Triethylammonium phosphate solution, volatile buffer, ~1.0 M in H₂O, Trimethylammonium acetate solution, volatile buffer, ~1.0 M in H₂O, Trimethylammonium phosphate solution, volatile buffer, ~1 M in H₂O, Tris-EDTA buffer solution, for molecular biology, concentrate, 100× concentrate, Tris-EDTA buffer solution, for molecular biology, pH 7.4, Tris-EDTA buffer solution, for molecular biology, pH 8.0, Trizma® acetate, ≥99.0% (NT), Trizma® base, ≥99.8% (T), Trizma® base, ≥99.8% (T), Trizma® base, for luminescence, ≥99.8% (T), Trizma® base, for molecular biology, ≥99.8% (T), Trizma® carbonate, ≥98.5% (T), Trizma® hydrochloride buffer solution, for molecular biology, pH 7.2, Trizma® hydrochloride buffer solution, for molecular biology, pH 7.4, Trizma® hydrochloride buffer solution, for molecular biology, pH 7.6, Trizma® hydrochloride buffer solution, for molecular biology, pH 8.0, Trizma® hydrochloride, ≥99.0% (AT), Trizma® hydrochloride, for luminescence, ≥99.0% (AT), Trizma® hydrochloride, for molecular biology, ≥99.0% (AT), and Trizma® maleate, ≥99.5% (NT).

The nanoemulsion HSV vaccine can comprise one or more emulsifying agents to aid in the formation of emulsions. Emulsifying agents include compounds that aggregate at the oil/water interface to form a kind of continuous membrane that prevents direct contact between two adjacent droplets. Certain embodiments of the present invention feature nanoemulsion vaccines that may readily be diluted with water or another aqueous phase to a desired concentration without impairing their desired properties.

4. Droplet Size

The nanoemulsion HSV vaccine of the present invention comprises droplets having an average diameter size of less than about 1,000 nm. In other embodiments of the invention, the droplet size has an average diameter of less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, or any combination thereof. In one embodiment, the droplets have an average diameter size greater than about 125 nm and less than or equal to about 600 nm. In a different embodiment, the droplets have an average diameter size greater than about 50 nm or greater than about 70 nm, and less than or equal to about 125 nm.

In one embodiment, the nanoemulsion HSV vaccine droplets have an average diameter selected from the group consisting of less than about 1000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, greater than about 50 nm, greater than about 70 nm, greater than about 125 nm, and any combination thereof.

D. Pharmaceutical Compositions

The nanoemulsion HSV vaccines of the invention may be formulated into pharmaceutical compositions that comprise the nanoemulsion HSV vaccine in a therapeutically effective amount and suitable, pharmaceutically-acceptable excipients for pharmaceutically acceptable delivery. Such excipients are well known in the art.

By the phrase "therapeutically effective amount" it is meant any amount of the nanoemulsion HSV vaccine that is effective in preventing, treating or ameliorating a disease caused by the HSV pathogen associated with the immunogen administered in the composition comprising the nanoemulsion HSV vaccine. By "protective immune response" it is meant that the immune response is associated with prevention, treating, or amelioration of a disease. Complete prevention is not required, though is encompassed by the present invention. The immune response can be evaluated using the methods discussed herein or by any method known by a person of skill in the art.

Intranasal administration includes administration via the nose, either with or without concomitant inhalation during administration. Such administration is typically through contact by the composition comprising the nanoemulsion HSV vaccine with the nasal mucosa, nasal turbinates or sinus cavity. Administration by inhalation comprises intranasal administration, or may include oral inhalation. Such administration may also include contact with the oral mucosa, bronchial mucosa, and other epithelia.

Exemplary dosage forms for pharmaceutical administration are described herein. Examples include but are not limited to liquids, ointments, creams, emulsions, lotions, gels, bioadhesive gels, sprays, aerosols, pastes, foams, sunscreens, capsules, microcapsules, suspensions, pessary, powder, semi-solid dosage form, etc.

The pharmaceutical nanoemulsion HSV vaccines may be formulated for immediate release, sustained release, controlled release, delayed release, or any combinations thereof, into the epidermis or dermis. In some embodiments, the formulations may comprise a penetration-enhancing agent. Suitable penetration-enhancing agents include, but are not limited to, alcohols such as ethanol, triglycerides and aloe compositions. The amount of the penetration-enhancing agent may comprise from about 0.5% to about 40% by weight of the formulation.

The nanoemulsion HSV vaccines of the invention can be applied and/or delivered utilizing electrophoretic delivery/ electrophoresis. Further, the composition may be a transdermal delivery system such as a patch or administered by a pressurized or pneumatic device (i.e., "gene gun"). Such methods, which comprise applying an electrical current, are well known in the art.

The pharmaceutical nanoemulsion HSV vaccines for administration may be applied in a single administration or in multiple administrations.

If applied topically, the nanoemulsion HSV vaccines may be occluded or semi-occluded. Occlusion or semi-occlusion may be performed by overlaying a bandage, polyoleofin film, article of clothing, impermeable barrier, or semi-impermeable barrier to the topical preparation.

An exemplary nanoemulsion adjuvant composition according to the invention is designated "$W_{80}5EC$" adjuvant. The composition of $W_{80}5EC$ adjuvant is shown in the table below (Table 1)H. The mean droplet size for the $W_{80}5EC$ adjuvant is ~400 nm. All of the components of the nanoemulsion are included on the FDA inactive ingredient list for Approved Drug Products.

TABLE 1

| $W_{80}5EC$ Formulation | |
|---|---|
| Function | $W_{80}5EC$-Adjuvant Mean Droplet Size ≈ 400 nm |
| Aqueous Diluent | Purified Water, USP |
| Hydrophobic Oil (Core) | Soybean Oil, USP (super refined) |
| Organic Solvent | Dehydrated Alcohol, USP (anhydrous ethanol) |
| Surfactant | Polysorbate 80, NF |
| Emulsifying Agent Preservative | Cetylpyridinium Chloride, USP |

The nanoemulsion adjuvants are formed by emulsification of an oil, purified water, nonionic detergent, organic solvent and surfactant, such as a cationic surfactant. An exemplary specific nanoemulsion adjuvant is designated as "60% $W_{80}5EC$". The 60% $W_{80}5EC$-adjuvant is composed of the ingredients shown in Table 2 below: purified water, USP; soybean oil USP; Dehydrated Alcohol, USP [anhydrous ethanol]; Polysorbate 80, NF and cetylpyridinium chloride, USP (CPCAII components of this exemplary nanoemulsion are included on the FDA list of approved inactive ingredients for Approved Drug Products.

TABLE 2

| Composition of 60% $W_{80}5EC$-Adjuvant (w/w %) | |
|---|---|
| Ingredients | 60% $W_{80}5EC$ |
| Purified Water, USP | 54.10% |
| Soybean Oil, USP | 37.67% |
| Dehydrated Alcohol, USP (anhydrous ethanol) | 4.04% |
| Polysorbate 80, NF | 3.55% |
| Cetylpyridinium Chloride, USP | 0.64% |

E. Stability of the Nanoemulsion HSV Vaccines of the Invention

The nanoemulsion HSV vaccines of the invention can be stable at about 40° C. and about 75% relative humidity for a time period of at least up to about 2 days, at least up to about 2 weeks, at least up to about 1 month, at least up to about 3 months, at least up to about 6 months, at least up to about 12 months, at least up to about 18 months, at least up to about 2 years, at least up to about 2.5 years, or at least up to about 3 years.

In another embodiment of the invention, the nanoemulsion HSV vaccines of the invention can be stable at about 25° C. and about 60% relative humidity for a time period of at least up least up to about 2 days, at least up to about 2 weeks, to about 1 month, at least up to about 3 months, at least up to about 6 months, at least up to about 12 months, at least up to about 18 months, at least up to about 2 years, at least up to about 2.5 years, or at least up to about 3 years, at least up to about 3.5 years, at least up to about 4 years, at least up to about 4.5 years, or at least up to about 5 years.

Further, the nanoemulsion HSV vaccines of the invention can be stable at about 4° C. for a time period of at least up to about 1 month, at least up to about 3 months, at least up to about 6 months, at least up to about 12 months, at least up to about 18 months, at least up to about 2 years, at least up to about 2.5 years, at least up to about 3 years, at least up to about 3.5 years, at least up to about 4 years, at least up to about 4.5 years, at least up to about 5 years, at least up to about 5.5 years, at least up to about 6 years, at least up to about 6.5 years, or at least up to about 7 years.

The nanoemulsion HSV vaccines of the invention can be stable at about −20° C. for a time period of at least up to about 1 month, at least up to about 3 months, at least up to about 6 months, at least up to about 12 months, at least up to about 18 months, at least up to about 2 years, at least up to about 2.5 years, at least up to about 3 years, at least up to about 3.5 years, at least up to about 4 years, at least up to about 4.5 years, at least up to about 5 years, at least up to about 5.5 years, at least up to about 6 years, at least up to about 6.5 years, or at least up to about 7 years.

These stability parameters are also applicable to nanoemulsion adjuvants and/or nanoemulsion HSV vaccines.

F. Methods of Manufacture

The nanoemulsions of the invention can be formed using classic emulsion forming techniques. See e.g., U.S. 2004/0043041. In an exemplary method, the oil is mixed with the aqueous phase under relatively high shear forces (e.g., using high hydraulic and mechanical forces) to obtain a nanoemulsion comprising oil droplets having an average diameter of less than about 1000 nm. Some embodiments of the invention employ a nanoemulsion having an oil phase comprising an alcohol such as ethanol. The oil and aqueous phases can be blended using any apparatus capable of producing shear forces sufficient to form an emulsion, such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In an exemplary embodiment, the nanoemulsions used in the methods of the invention comprise droplets of an oily discontinuous phase dispersed in an aqueous continuous phase, such as water or PBS. The nanoemulsions of the invention are stable, and do not deteriorate even after long storage periods. Certain nanoemulsions of the invention are non-toxic and safe when swallowed, inhaled, or contacted to the skin of a subject.

The compositions of the invention can be produced in large quantities and are stable for many months at a broad range of temperatures. The nanoemulsion can have textures ranging from that of a semi-solid cream to that of a thin lotion, to that of a liquid and can be applied topically by any pharmaceutically acceptable method as stated above, e.g., by hand, or nasal drops/spray.

As stated above, at least a portion of the emulsion may be in the form of lipid structures including, but not limited to, unilamellar, multilamellar, and paucliamellar lipid vesicles, micelles, and lamellar phases.

The present invention contemplates that many variations of the described nanoemulsions will be useful in the methods of the present invention. To determine if a candidate nanoemulsion is suitable for use with the present invention, three criteria are analyzed. Using the methods and standards described herein, candidate emulsions can be easily tested to determine if they are suitable. First, the desired ingredients are prepared using the methods described herein, to determine if a nanoemulsion can be formed. If a nanoemulsion cannot be formed, the candidate is rejected. Second, the candidate nanoemulsion should form a stable emulsion. A nanoemulsion is stable if it remains in emulsion form for a sufficient period to allow its intended use. For example, for nanoemulsions that are to be stored, shipped, etc., it may be desired that the nanoemulsion remain in emulsion form for months to years. Typical nanoemulsions that are relatively unstable, will lose their form within a day. Third, the candidate nanoemulsion should have efficacy for its intended use. For example, the emulsions of the invention should kill or disable HSV virus to a detectable level, or induce a protective immune response to a detectable level. The nanoemulsion of the invention can be provided in many different types of containers and delivery systems. For example, in some embodiments of the invention, the nanoemulsions are provided in a cream or other solid or semi-solid form. The nanoemulsions of the invention may be incorporated into hydrogel formulations.

The nanoemulsions can be delivered (e.g., to a subject or customers) in any suitable container. Suitable containers can be used that provide one or more single use or multi-use dosages of the nanoemulsion for the desired application. In some embodiments of the invention, the nanoemulsions are provided in a suspension or liquid form. Such nanoemulsions can be delivered in any suitable container including spray bottles and any suitable pressurized spray device. Such spray bottles may be suitable for delivering the nanoemulsions intranasally or via inhalation.

In an exemplary method of the invention for preparing a nanoemulsion HSV vaccine useful for the treatment or prevention of an HSV infection in humans, the method comprises: (a) synthesizing in a eukaryotic host one or more full length or immunogenic fragment HSV surface antigens utilizing recombinant DNA genetics vectors and constructs, wherein the HSV surface antigen is selected from the group consisting of HSV gB, HSV gC, HSV gD, and HSV gE; (b) isolating the one or more surface antigens or immunogenic fragments thereof from the eukaryotic host; and (c) formulating the one or more surface antigens with an oil-in-water nanoemulsion. The eukaryotic host can be, for example, a mammalian cell or a yeast cell. In another embodiment of the invention, the method comprises (a) obtaining isolated whole HSV virus; and (b) formulating the HSV virus with an oil-in-water nanoemulsion. In yet another embodiment, both whole HSV virus and isolated HSV antigens can be utilized in the nanoemulsion HSV vaccines of the invention. The HSV can be HSV-1 or HSV-2.

These nanoemulsion-containing containers can further be packaged with instructions for use to form kits.

The invention is further described by reference to the examples, which are provided for illustration only. The invention is not limited to the examples, but rather includes all variations that are evident from the teachings provided herein. All publicly available documents referenced herein, including but not limited to U.S. patents, are specifically incorporated by reference.

Example 1

The purpose of this example was to describe preparation of a nanoemulsion to be used in a nanoemulsion HSV vaccine.

To manufacture the nanoemulsion, the water soluble ingredients are first dissolved in water. The soybean oil is then added and the mixture is mixed using high shear homogenization and/or microfluidization until a viscous white emulsion is formed. The emulsion may be further diluted with water to yield the desired concentration of emulsion or cationic surfactant.

The nanoemulsion (NE) composition was formulated according to Table 3.

TABLE 3

Nanoemulsion composition

| Component | Concentration v/v |
|---|---|
| Water | 84.7% |
| Soybean Oil | 12.6% |
| Ethanol | 1.35% |
| Polysorbate 80 | 1.18% |
| Cetylpyridinium chloride (CPC) | 0.2% |

The nanoemulsion can then be combined with one or more HSV immunogens to form a nanoemulsion HSV vaccine according to the invention.

Example 2

The purpose of this example is to describe exemplary nanoemulsions useful as adjuvants for an HSV vaccine.

A total of 10 nanoemulsion formulations were prepared: $W_{80}5EC$ alone, six $W_{80}5EC$+Poloxamer 407 and Poloxamer 188 (P407 and P188) formulations as well as two $W_{80}5EC$+Chitosan and one $W_{80}5EC$+Glucan formulation have been produced and assessed for stability over 2 weeks under accelerated conditions at 40° C. (Table 4). All 10 nanoemulsions were stable for at least 2 weeks at 40° C.

TABLE 4

$W_{80}5EC$ Formulations

| Nanoemulsion (lot) | Ratios: CPC:Tween:Poloxamer | Method of Addition of Poloxamer | Particle Size (nm) | Zeta Potential (mV) | pH |
|---|---|---|---|---|---|
| $W_{80}5EC$ | 1:6 | — | 450 | 60 | 4.9 |
| $W_{80}5EC$ + 3% P407 | 1:6 | External | 500 | 56 | 5.9 |
| $W_{80}5EC$/P407 | 1:5:1 | Internal | 391 | 46 | 5.5 |
| $W_{80}5EC$/P407 | 1:1:5 | Internal | 253 | 36 | 5.2 |
| $W_{80}5EC$/P188 | 1:5:1 | Internal | 526 | 54 | 5.1 |
| $W_{80}5EC$/P188 | 1:3:3 | Internal | 416 | 54 | 5.7 |
| $W_{80}5EC$/P188 | 1:1:5 | Internal | 370 | 47 | 5.2 |
| $W_{80}5EC$ + 0.3% Chitosan LMW | 1:6 | External | 505 | 60 | 5.7 |
| $W_{80}5EC$ + 0.3% Chitosan MMW | 1:6 | External | 523 | 60 | 5.4 |
| $W_{80}5EC$ + 0.03% β(1,3) Glucan | 1:6 | External | 491 | 41 | 6.3 |

The following formulations are exemplary nanoemulsions useful in the HSV vaccines of the invention: (1) Formulation 1, $W_{80}5EC$ (NE80), comprising: (a) CPC/Tween 80 (ratio of 1:6), and (b) Particle size ~500 nm (Table 5); and Formulation 2, $W_{80}P_{188}5EC$ (NE188), comprising: (a) CPC/Tween 80/P188 (ratio of 1:1:5), (b) Particle size ~300 nm (Table 6).

TABLE 5

Formulation 1
Composition of 60% $W_{80}5EC$ adjuvant

| Ingredient | w/w % |
|---|---|
| Distilled water | 54.1 |
| CPC | 0.64 |
| Tween 80 | 3.55 |
| Ethanol | 4.04 |
| Soybean oil | 37.7 |

TABLE 6

Formulation 2
Composition of 60% $W_{80}P_{188}5EC$ adjuvant

| Ingredient | w/w % |
|---|---|
| Distilled water | 54.1 |
| CPC | 0.64 |
| Tween 80 | 0.6 |
| Poloxamer 188 | 3 |
| Ethanol | 4.03 |
| Soybean oil | 37.7 |

Example 3

The purpose of this example was to demonstrate the associated of a nanoemulsion with viral antigen.

Materials and Methods: Transmission Electron Micrographs and Sectioning Technique: Twenty mL of the nanoemulsion adjuvant alone or with Fluzone® was fixed with 1% (w/v) osmium tetroxide solution. The fixed preparations were mixed with histogel in 1:10 ratio to form a solid mass. The solid mixture of was sliced into thin 1 mm slices and rinsed with double distilled deionizer water. The cross-sectioned samples were dehydrated with ascending concentrations (30%, 50%, 70%, 90%, 100%) of component A of the Durcupan® kit (Fluka, EM #14020) in double distilled deionizer water. These samples were transferred into embedding solution (mixture of components A, B, C and D) of the Durcupan® kit. The embedded samples were sectioned to a 75 nm thickness and placed on 300 mesh carbon-coated copper grid. The sections on the grids were stained with saturated uranyl acetate in distilled and deionizer water (pH 7) for 10 minutes followed by lead citrate for 5 minutes. The samples were viewed with a Philips CM-100 TEM equipped with a computer controlled compustage, a high resolution (2K×2K) digital camera and digitally imaged and captured using X-Stream imaging software (SEM Tech Solutions, Inc., North Billerica, Mass.).

Results: Electron Micrographs: Cross sectioned TEM of 20% $W_{80}5EC$ nanoemulsion showed nanoemulsion droplets with a uniform inner core material. Nanoemulsion vaccine containing 30 μg of HA shows discrete antigen materials/particles inside the oil core of the droplets that represent the Fluzone® antigens. Since the antigen is incorporated in the core, and is surrounded by the core material, it is protected from staining by the electron dense stain. This leads to a white counter staining effect in the core. The localization of the antigen within the core shields the antigen-sensitive protein subunits in the emulsion, and may protect the antigen from degradation, and thus enhancing stability. There are very few Fluzone® particles outside of the NE particles that were stained dark in color (FIGS. 1a and 1b).

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

FULL CITATIONS FOR DOCUMENTS REFERRED IN THE SPECIFICATION

1. Allen S, Mott K, Zandian M., Immunization with different viral antigens alters the pattern of T cell exhaustion and latency in herpes simplex virus type-1 infection mice. J. Virol. 2010. 84:12315-12324.
2. Ashley, R, Mertz, G, Clark H, et al. Humoral immune response to herpes simplex virus type 2 glycoproteins in patients receiving a glycoprotein subunit vaccine. J. Virol. 1985. 56:475-481.
3. Awasthi, S, Lubinski J, Friedman, H. Immunization with HSV-1 glycoprotein C prevents immune evasion from complement and enhances the efficacy of an HSV-1 glycoprotein S subunit vaccine. Vaccine. 2009. 27:6845-6853.
4. Awasthi, S, Lubinski, J, Shaw, C, Barett, S, et al. HSV-2 glycoprotein C subunit immunization with glycoprotein D improves the protection of dorsal root ganglia in mice and reduces the frequency of recurrent vaginal shedding of HSV-2 DNA in guinea pigs compared to glycoprotein D alone. J. Virol. 2011. 1128/00849-11
5. Bernstein D, Earwood J, Bravo F, et al. Effects of herpes simplex virus type 2 glycoprotein vaccines and CLDC adjuvant on genital herpes infection in the guinea pig. Vaccine. 2011. 29:2071-2078.
6. Bielinska, A, Gerber M, Blanco L, et al. Induction of Th17 cellular immunity with a novel nanoemulsion adjuvant. 2010. Crit. Rev Immunol. 30:189-199.
7. Chan T, Barra N, et al. Innate and adaptive immunity against herpes simplex virus type 2 in the genital mucosa. J Repro Immunol. 2011. 88:210-218.
8. Chang, Y J, Jiang M, Lubinski, J., et al. Implication for herpes simplex virus strategies based on antibodies produced to herpes simplex virus type 1 glycoprotein gC immune evasion domains. Vaccine. 2005. 23:4658-4665.
9. Conti H R, Shen F, et al., Th17 and IL-17 receptor signaling are essential for mucosal host defenses against oral candidiasis. J Exp Med. 2009. 206:299-311.
10. Corey, L, Langenberg A, Ashley R, et al. Recombinant glycoprotein vaccine for the prevention of genital HSV-2 infection; two randomized controlled trials. JAMA. 1999. 281:331-340.
11. Dasgupta, G, BenMohamed, L. Of mice and humans: how reliable are animal models for evaluation of herpes CD8+-T cells epitopes-based immunotherapeutic vaccine candidates. Vaccine. 2011. 29:5824-5836.
12. Dasgupta, G, Chentoufi A, Nesburn A, et al. New concepts in herpes simplex virus vaccine development: notes from the battlefield. Expert Rev Vaccine. 2009. 8:1023-1035.
13. DeLyrica E, Raymond W R, et al., Vaccination of mice with H pylori induces a strong Th-17 response and immunity that is neutrophil dependent. Gastroent. 2009. 136:247-256.
14. Ghiasi, H, Kaiwar R., et al. Baculovirus-expressed glycoprotein E (gE) of herpes simplex virus type 1 (HSV-1) protects mice from lethal intraperitoneal and lethal ocular HSV-1 challenge. 1992. Virol. 188:469-476.
15. Hamouda T, Chepurnov A, Mank N, et al. Efficacy, immunogenicity and stability of a novel intranasal nanoemulsion adjuvanted influenza vaccine in a murine model. Hum Vaccine. 2010. 6:585-594.
16. Han J, Schleiss M. It is time to examine the role of host cytokine response in neonatal herpes simplex virus infection. Future Virol. 2011. 6:679-681.
17. Judson, K, Lubinski, J, Jiang, M, et al. Blocking immune evasion as a novel approach for prevention and treatment of herpes simplex virus infection. J. Virol. 2003. 77:12639-12645.
18. Lindell D, Morris S, White M, et al. A novel inactivated intranasal respiratory syncytial virus vaccine promotes viral clearance without Th2 associated vaccine-enhanced disease. PLoS One. 2011. 7:e21823.
19. Makidon, P, Bielinska, A, Nigavekar, S, et al. Preclinical evaluation of a novel nanoemulsion-based hepatitis B mucosal vaccine. PLOS-One. 2008. 3:e2954.
20. McGowin C, Pyles R. Mucosal treatment for herpes simplex virus: insights on targeted immunoprophylaxis and therapy. Future Microbiol. 2010. 5:15-22.
21. Parr E, Parr M. Immune response and protection against vaginal infection after nasal or vaginal immunization with attenuated herpes simplex virus type-2. Immunol. 1999. 98:639-645.
22. Roizman, B, Spears P. Herpes simplex viruses and their replication. In Fields, B. et al. Fields Virology. 1996. 2231-2296. Lippincott. N.Y.
23. Thatte A, DeWitte-Orr J, Lichty K, et al. A critical role for IL-15 in TLR-mediated innate antiviral immunity against genital HSV-2 infection. Immunol and Cell Biol. 2011.1-7.
24. Zarling, J, Moran P, et al. Herpes Simplex Virus (HSV)-specific proliferative and cytotoxic T-cell responses in humans immunized with an HSV type 2 glycoprotein subunit vaccine. J. Virol. 1988. 62:4481-4485.
25. Dobson C B, Itzhaki R F (1999). "Herpes simplex virus type 1 and Alzheimer's disease". Neurobiol. Aging 20 (4): 457-65.

26. Pyles R B (November 2001). "The association of herpes simplex virus and Alzheimer's disease: a potential synthesis of genetic and environmental factors" (PDF). Herpes 8 (3): 64-8.

The invention claimed is:

1. A mucosal herpes simplex virus (HSV) vaccine composition consisting essentially of:
   (a) an immune enhancing nanoemulsion suitable for mucosal administration, wherein the nanoemulsion comprises:
      (i) droplets having an average diameter of less than about 600 nm;
      (ii) an aqueous phase;
      (iii) about 12.6% of a pharmaceutically acceptable oil;
      (iv) about 1.18% of at least one surfactant, wherein the surfactant is Polysorbate 80, Polysorbate 20, or a combination thereof;
      (v) about 1.35% of at least one organic solvent, wherein the organic solvent is an alcohol; and
      (vi) about 0.2% of a cationic surfactant, wherein the cationic surfactant is cetylpyridinium chloride (CPC) or dioctyl dimethyl ammonium chloride; and
   (b) a combination comprising an isolated HSV gD antigen and an isolated HSV gB antigen within the nanoemulsion, wherein (i) the HSV gD antigen is an HSV-1 gD, HSV-2 gD, or an immunogenic fragment of HSV-1 gD or HSV-2 gD; and (ii) the HSV gB antigen is an HSV-1 gB, HSV-2 gB, or an immunogenic fragment of HSV-1 gB or HSV-2 gB.

2. The mucosal HSV vaccine composition of claim 1, wherein one or more HSV antigens further comprise nucleotide modifications denoting attenuating phenotypes.

3. The mucosal HSV vaccine composition of claim 1, wherein at least one HSV antigen is present in a fusion protein.

4. The mucosal HSV vaccine composition of claim 1, wherein the composition comprises a HSV-2 gB antigen or an immunogenic fragment thereof, and a HSV-2 gD antigen or an immunogenic fragment thereof.

5. The mucosal HSV vaccine composition of claim 1, wherein the immune enhancing nanoemulsion produces an immune response which is a Th1, Th2 and/or Th17 immune response.

6. The mucosal HSV vaccine composition of claim 1, wherein the nanoemulsion comprises droplets having an average diameter size of from about 300 nm up to about 600 nm.

7. The mucosal HSV vaccine composition of claim 1 further comprising an additional adjuvant.

8. The mucosal HSV vaccine composition of claim 1 further comprising a pharmaceutically acceptable carrier.

9. The mucosal HSV vaccine composition of claim 1, wherein the vaccine composition is formulated for administration either intravaginally or intranasally.

10. A method for preparing a mucosal herpes simplex virus (HSV) vaccine useful for the treatment or prevention of an HSV infection in humans comprising:
    (a) synthesizing in a eukaryotic host one or more recombinant, full length or immunogenic fragment HSV antigens, wherein the HSV antigen is selected from the group consisting of HSV-1 gB, HSV-2 gB, HSV-1 gD, and HSV-2 gD;
    (b) isolating the one or more antigens or immunogenic fragments thereof from the eukaryotic host; and
    (c) formulating a combination comprising an isolated HSV gD antigen and an isolated HSV gB antigen with an oil-in-water nanoemulsion, wherein the nanoemulsion, or a dilution thereof, comprises:
       (i) droplets having an average diameter of less than about 600 nm;
       (ii) an aqueous phase;
       (iii) about 63% of a pharmaceutically acceptable oil;
       (iv) about 5.9% of at least one surfactant, wherein the surfactant is Polysorbate 80, Polysorbate 20, or a combination thereof;
       (v) about 6.75% of at least one organic solvent, wherein the organic solvent is an alcohol; and
       (vi) about 1% of a cationic surfactant.

11. The method according to claim 10, wherein the eukaryotic host is a mammalian cell.

12. The method according to claim 10, wherein the eukaryotic host is a yeast cell.

13. The method according to claim 10, wherein the HSV is HSV-1.

14. The method according to claim 10, wherein the HSV is HSV-2.

15. A herpes simplex virus (HSV) mucosal subunit vaccine composition consisting essentially of:
    (a) an immune enhancing nanoemulsion, wherein the nanoemulsion comprises:
       (i) droplets having an average diameter of less than about 600 nm;
       (ii) an aqueous phase;
       (iii) about 63% of a pharmaceutically acceptable oil;
       (iv) about 5.9% of at least one surfactant, wherein the surfactant is Polysorbate 80, Polysorbate 20, or a combination thereof;
       (v) about 6.75% of at least one organic solvent, wherein the organic solvent is an alcohol; and
       (vi) about 1.0% of a cationic surfactant, wherein the cationic surfactant is cetylpyridinium chloride (CPC) or dioctyl dimethyl ammonium chloride;
    (b) a combination comprising an isolated multivalent HSV gD antigen and an isolated multivalent HSV gB antigen within the nanoemulsion, wherein (i) the HSV gD antigen is an HSV-1 gD, HSV-2 gD, or an immunogenic fragment of HSV-1 gD or HSV-2 gD; and (ii) the HSV gB antigen is an HSV-1 gB, HSV-2 gB, or an immunogenic fragment of HSV-1 gB or HSV-2 gB
    wherein the immune enhancing nanoemulsion is diluted to about 20% in an aqueous phase, thereby making it suitable for mucosal administration.

16. The HSV mucosal subunit vaccine composition of claim 15, further comprising an additional adjuvant.

17. The HSV mucosal subunit vaccine composition of claim 15, further comprising at least one pharmaceutically acceptable carrier.

18. The HSV mucosal subunit vaccine composition of claim 15, wherein the vaccine composition is administered either intravaginally or intranasally.

19. The HSV mucosal vaccine composition of claim 1, wherein the HSV gD antigen or HSV gD antigen is a recombinant antigen.

20. The HSV mucosal subunit vaccine composition of claim 15, wherein the HSV gD antigen or HSV gD antigen is a recombinant antigen.

21. The HSV mucosal vaccine composition of claim 1, wherein the HSV gD antigen is HSV-2 gD.

22. The HSV mucosal vaccine composition of claim 1, wherein the HSV gD antigen is HSV-2 gD and the HSV gB antigen is HSV-2 gB.

23. The HSV mucosal vaccine composition of claim 9, wherein the vaccine composition is formulated for intranasal administration, and wherein intranasal administration of the vaccine composition to a subject induces an immune response.

24. The HSV mucosal subunit vaccine composition of claim 15, wherein the vaccine composition is formulated for intranasal administration, and wherein intranasal administration of the vaccine composition to a subject induces an immune response.

25. The HSV mucosal vaccine composition of claim 1, wherein the nanoemulsion comprises less than about 100 µg of HSV antigen.

26. The HSV mucosal subunit vaccine composition of claim 15, wherein the HSV gD antigen is HSV-2 gD.

27. The HSV mucosal subunit vaccine composition of claim 15, wherein the HSV gD antigen is HSV-2 gD and the HSV gB antigen is HSV-2 gB.

28. The HSV mucosal vaccine composition of claim 1, wherein the cationic surfactant is cetylpyridinium chloride.

* * * * *